United States Patent
Belden et al.

(10) Patent No.: US 8,922,636 B1
(45) Date of Patent: Dec. 30, 2014

(54) SYNTHETIC APERTURE IMAGING FOR FLUID FLOWS

(75) Inventors: Jesse L. Belden, Providence, RI (US); Tadd T. Truscott, Provo, UT (US); Alexandra H. Techet, Charlestown, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 682 days.

(21) Appl. No.: 13/213,866

(22) Filed: Aug. 19, 2011

Related U.S. Application Data

(60) Provisional application No. 61/375,510, filed on Aug. 20, 2010.

(51) Int. Cl.
  *H04N 7/18* (2006.01)
(52) U.S. Cl.
  USPC .......................................................... 348/77
(58) Field of Classification Search
  None
  See application file for complete search history.

(56) References Cited

U.S. PATENT DOCUMENTS

| | | | |
|---|---|---|---|
| 2005/0062954 A1* | 3/2005 | Wieneke | 356/28 |
| 2009/0133480 A1* | 5/2009 | Ivanov et al. | 73/64.51 |
| 2011/0115485 A1* | 5/2011 | Subbarao | 324/309 |

* cited by examiner

*Primary Examiner* — William C Vaughn, Jr.
*Assistant Examiner* — Eileen Adams
(74) *Attorney, Agent, or Firm* — James M. Kasischke; Michael P. Stanley

(57) ABSTRACT

A synthetic aperture three-dimensional fluid flow imaging apparatus is provided. The apparatus includes a plurality of cameras. At least two of the cameras are oriented to view a volume along mutually non-parallel directions. The cameras are connected to a programmable computer. The computer captures images from the cameras to generate three dimensional intensity fields. The computer can refocus the images on at least one refocus plane to generate reconstructed three dimensional intensity fields on a plane within the volume. Intensity field cross-correlation is performed on the reconstructed three dimensional intensity fields to extract velocity fields within the volume. The velocity fields represent velocities of objects or fluid phases within the volume. These velocity fields can be recorded for later use.

14 Claims, 13 Drawing Sheets

SYNTHETIC APERTURE IMAGING FOR FLUID FLOWS

This application claims the benefit of U.S. Provisional Application No. 61/375,510, filed Aug. 20, 2010 and which is entitled SYNTHETIC APERTURE PARTICLE IMAGE VELOCIMETRY by JESSE L. BELDEN, TADD T. TRUSCOTT and ALEXANDRA H. TECHET.

STATEMENT OF GOVERNMENT INTEREST

The invention described herein may be manufactured and used by or for the Government of the United States of America for Governmental purposes without the payment of any royalties thereon or therefor.

CROSS REFERENCE TO OTHER PATENT APPLICATIONS

None.

BACKGROUND OF THE INVENTION (1) Field of the Invention

The invention relates to systems and methods for measuring particle velocities in general and particularly to systems and methods that employ synthetic aperture methods to measure particle velocities.

(2) Description of the Prior Art

Efforts for resolving three-dimensional velocity fields are justified by the need to experimentally resolve flows that are highly three-dimensional and to validate numerical simulations of complex flows. The ability to spatio-temporally resolve flow features from small to large scales in arbitrarily large volumes is the goal of any three dimensional particle image velocimetry system. Of course, there have been many roadblocks to achieving all of these goals with a single system, and compromises must be made. Two-dimensional particle image velocimetry (2D PIV) is the most pervasive method for resolving velocity fields, thus it is not surprising that recent efforts to resolve three dimensional flow fields have extended many of the fundamentals of two dimensional particle image velocimetry to the third dimension.

Several methods exist for resolving three dimensional particle fields, or any three dimensional scenes for that matter, but the methods of data acquisition seem to fall into three broad categories: multiple-viewpoints, holography and internal optics alteration.

One of the earliest, but still frequently utilized, methods for three dimensional particle image velocimetry is two camera stereoscopic particle image velocimetry, which is primarily used to resolve the third component of velocity within a thin light sheet. A three dimensional particle tracking velocimetry (PTV) method is known which resolves the location of individual particles imaged by two, three or four cameras in a stereoscopic configuration. They report measurements in a large volume (e.g. 200×160×50 mm$^3$), but with very low seeding density ($\approx$1000 particles). Through precise calibration and knowledge of the imaging geometry, the particle field can be reconstructed. More recently, improvements to PTV methods have been made. In general, low seeding density is a typical limitation of PTV, yielding low spatial resolution in the vector fields.

Another technique which makes use of multiple viewpoints is defocusing digital particle image velocimetry (DDPIV). In theory, DDPIV capitalizes on the defocus blur of particles by placing an aperture with a defined pattern (usually pinholes arranged as an equilateral triangle) before the lens, which is a form of coded aperture imaging. The spread between three points generated by imaging a single particle corresponds to the distance from the camera along the Z dimension. In practice, the spread between particles is achieved using three off-axis pinhole cameras which causes a single point in space to appear at separate locations relative to the sensor of each camera. The images from all three camera sensors are superimposed onto a common coordinate system, an algorithm searches for patterns which form an equilateral triangle, and based on size and location of the triangle the three dimensional spatial coordinates of the point can be resolved. A main limitation of this technique appears to be seeding density, because the equilateral triangles formed by individual particles must be resolved to reconstruct the particle field. Simulations with seeding density of 0.038 particles per pixel (ppp) in a volume size of 100×100×100 mm$^3$ have been reported, and experiments with seeding density of 0.034 ppp in a volume size of 150×150×150 mm$^3$. The technique has also been efficiently implemented with a single camera using an aperture with color-coded pinholes, to measure velocity fields in a buoyancy driven flow in a 3.35×2.5×1.5 mm$^3$ volume with seeding density$\approx$0.001 ppp.

Tomographic-PIV also uses multiple viewpoints (usually 3-6 cameras) to obtain three dimensional velocity fields. Optical tomography reconstructs a three dimensional intensity field from the images on a finite number of cameras. The intensity fields are then subjected to three dimensional particle image velocimetry cross-correlation analysis. The seeding density for tomographic-PIV seems to be the largest attainable of the existing techniques. Simulations show volumetric reconstruction with seeding density of 0.05 ppp, and recent tomographic-PIV experiments typically have seeding density in the range of 0.02-0.08 ppp. The viewable depth of volumes in tomographic-PIV is typically three to five times smaller than the in-plane dimensions.

Holographic PIV (HPIV) is a technique in which the three-dimensional location of particles in a volume is deduced from the interference pattern of the light waves emanating from particles and the coherent reference wave that is incident upon the field. The nature of the interference pattern is used to back out information about the phase of light diffracted from objects in the volume, which is related to the distance of the objects from the sensor (i.e. depth in the volume). Holographic PIV makes use of this principle to image particle-laden volumes of fluids, and extract information about location of particles in the volume. In holography, the size of the observable volume is ultimately limited by the size and spatial resolution of the recording device. Very high resolution measurements of turbulent flow in a square duct using film-based HPIV have been reported, where particles were seeded to a reported density of 1-8 particles/mm$^3$ in a volume measuring 46.6×46.6×42.25 mm$^3$. Although film has much better resolution and is larger than digital recording sensors, difficulties of film based holographic PIV have been extensively cited, which have likely prevented the method from being widely utilized. In contrast, digital Holographic PIV is more readily usable, but is often limited to small volumes and low seeding density. A digital hybrid HPIV method has been implemented which allows for measurement in volumes with larger depth, but the size of the in-plane dimensions are limited by the physical size of the digital sensor, and seeding density remains low. Recent results of measurements in a turbulent boundary layer with increased seeding density (0.014 ppp) in a volume measuring 1.5×2.5×1.5 mm$^3$ have been presented.

Also known in the prior art is Stroke, U.S. Pat. No. 3,785,262, which is said to disclose a method and apparatus for synthesizing large-aperture optics by exposure of a single photographic plate either successively or simultaneously through small-aperture optics. The technique represents the extension of the "synthetic-aperture radio telescope" principle to the optical domain by the relatively simple photographic synthesis of a "high-resolution" image in a single photograph, exposed either successively through sets of small "low-resolution" apertures successively placed to generate the spatial frequency components of the desired large aperture, or exposed simultaneously through a set of small "low-resolution" apertures having such optical characteristics and being so arranged as to generate the spatial frequency components of the desired large aperture.

Also known in the prior art is Kirk, U.S. Pat. No. 5,379,133, which is said to disclose an apparatus, a system, and a method wherein a synthetic aperture based sequence of image samples are generated with respect to a subject to be stereoscopically imaged. These sample images are presented to the spaced inputs of a holographic integrated combiner screen to be presented at an output aperture in laterally spaced mutual positioning. That spacing is selected, in one aspect, as one-half of the interpupillary distance of human eyes and thus binocular stereoscopic viewing at the aperture is achieved. The combiner screen may be utilized in conjunction with a holographic optical image combiner architecture which additionally employs a lens assembly such as a projecting lens to generate multi-zone outputs, each zone of which may be presented for stereoscopic viewing at a discrete viewing station. Correction for chromatic aberration of the holographic optical components is described.

Also known in the prior art is Adrian et al., U.S. Pat. No. 5,548,419, which is said to disclose a holographic particle image velocimeter that employs stereoscopic recording of particle images, taken from two different perspectives and at two distinct points in time for each perspective, on a single holographic film plate. The different perspectives are provided by two optical assemblies, each including a collecting lens, a prism and a focusing lens. Collimated laser energy is pulsed through a fluid stream, with elements carried in the stream scattering light, some of which is collected by each collecting lens. The respective focusing lenses are configured to form images of the scattered light near the holographic plate. The particle images stored on the plate are reconstructed using the same optical assemblies employed in recording, by transferring the film plate and optical assemblies as a single integral unit to a reconstruction site. At the reconstruction site, reconstruction beams, phase conjugates of the reference beams used in recording the image, are directed to the plate, then selectively through either one of the optical assemblies, to form an image reflecting the chosen perspective at the two points in time.

Also known in the prior art is Raffel et al., U.S. Pat. No. 5,610,703, which is said to disclose a digital particle image velocimetry (DPIV) method for contactless measurement of three dimensional flow velocities comprising the steps of seeding a flow with tracer particles; repeatedly illuminating a plane-like interrogation volume of the seeded flow; projecting the repeatedly illuminated interrogation volume onto at least a photo sensor in a projection direction for recording pictures of the illuminated interrogation volume; and determining the three dimensional flow velocities from the pictures of the repeatedly illuminated interrogation volume recorded by the photo sensor. The plane-like interrogation volume of the invention comprises at least two partial volumes positioned parallel to each other with regard to the projection direction. The step of repeatedly illuminating the interrogation volume comprises the step of illuminating the partial volumes in such a way that the pictures of different partial volumes are distinguishable from each other. The step of determining the three dimensional flow velocities of the flow comprises the steps of calculating a local autocorrelation function of a double exposed picture of the same partial volume, or calculating a local cross-correlation function between two separate pictures of the same partial volume, calculating a local cross-correlation function between two pictures of two different partial volumes, determining the sign of the out-of-plane component of the local flow velocities by using the location of a peak of the local cross-correlation function between the two pictures of the two different partial volumes, and determining the magnitude of the out-of-plane component of the local flow velocities by using the peak heights of peaks of both local correlation functions.

Also known in the prior art is McDowell et al., U.S. Pat. No. 5,905,568, which is said to disclose a system and a method for measuring three-dimensional velocities at a plurality of points in a fluid employing at least two cameras, positioned approximately perpendicular to one another. The cameras are calibrated to accurately represent image coordinates in world coordinate system. The two-dimensional views of the cameras are recorded for image processing and centroid coordinate determination. Any overlapping particle clusters are decomposed into constituent centroids. The tracer particles are tracked on a two-dimensional basis and then stereo matched to obtain three-dimensional locations of the particles as a function of time so that velocities can be measured therefrom. The stereo imaging velocimetry technique of the present invention provides a full-field, quantitative, three-dimensional map of any optically transparent fluid which is seeded with tracer particles.

Also known in the prior art is Meng et al., U.S. Pat. No. 6,496,262, which is said to disclose a holographic particle image velocimetry (HPIV) system that employs holograms of two time-separated particle fields, illuminated by separate reference beams on a single recording medium. 90-degree scattering is utilized for the object wave, in order to improve Numerical Aperture and resolve the third dimension of the hologram. The proposed HPIV system then uses substantially the same optical geometry for the reconstruction process. A CCD camera is utilized to extract particle subimages, thin slice by thin slice, and a centroid-finding algorithm is applied to extract centroid locations for each volume. The concise cross correlation (CCC) algorithm for extracting velocity vector fields from the centroid data is an important enabling feature of the proposed system. Correlations are calculated between subsets of centroids representing the images or cubes, and velocity vectors are computed from the individual correlations. Higher spatial resolution can also be obtained by pairing particle centroids individually.

Also known in the prior art is Schaller, U.S. Pat. No. 6,525,822, which is said to disclose a three-dimensional particle image velocimetry method, in which a stream system containing light-scattering particles is exposed continuously over a certain period or at least two discrete points in time using a laser light sheet, and a hologram is produced and evaluated. Increased accuracy in determining velocity is achieved by evaluating the hologram with regard to its phase information interferometrically by using a reconstruction wave and superimposing a reference wave.

Also known in the prior art is Japanese patent application publication JP2006058321A1, which is said to disclose a three-dimensional confocal microscopic system designed such that images used for micro PIV are acquired at the same focusing position by using accurate position information from an actuator. The three-dimensional confocal microscopic system includes: a confocal scanner for acquiring the slice images of a micro conduit as confocal images via a microscope; a video camera for outputting the image data of the confocal images; an actuator for moving the focusing position of the objective lens of the microscope in the direction of its optical axis; a control section for generating a scanning waveform signal for scanning the objective lens in the direction of the optical axis via the actuator; and an image processing section for calculating the speed of a fluid in the micro conduit on the basis of at least the two image data acquired by the video camera. Based upon a position signal output from the actuator, the system acquires at least the two images in a prescribed position in the micro conduit.

There is a need for improved particle image velocimetry in three dimensions.

SUMMARY OF THE INVENTION

A primary objective of the present invention is to provide a synthetic aperture particle three-dimensional image velocimetry apparatus having at least one refocus plane.

It is also a primary objective of the present invention to provide synthetic aperture three-dimensional (3D) imaging for fluid flows.

It is also an objective of the present invention to produce a synthetic aperture three dimensional imaging apparatus having a plurality of cameras.

It is yet another objective of the present invention to provide apparatus for imaging multiple phase fluid flows.

According to one aspect, the invention features a synthetic aperture particle three-dimensional (3D) image velocimetry apparatus. The apparatus comprises a plurality of image recording devices. At least two of said plurality of image recording devices are oriented so as to view a volume to be imaged along mutually non-parallel directions. A data processing apparatus based on a general purpose programmable computer is configured to operate under control of a set of instructions recorded on a machine readable medium. When operating under control of said set of instructions, said data processing apparatus is configured to perform the steps of: capturing a plurality of images using said at least two image recording devices oriented along mutually non-parallel directions to generate three dimensional intensity fields; refocusing said plurality of images on at least one refocus plane in the field of view of each image recording device to generate reconstructed three dimensional intensity fields on a plane placed at a location within said volume to be imaged. performing intensity field cross-correlation on said reconstructed three dimensional intensity fields to extract therefrom velocity fields within said volume to be imaged, said velocity fields representing velocities of objects or fluid phases within the volume to be imaged; and recording said velocity fields for later use.

In one embodiment, the image recording devices are cameras.

In another embodiment, the plurality of image recording devices are controlled by said general purpose programmable computer when operating under control of said set of instructions recorded on said machine readable medium.

In yet another embodiment, the synthetic aperture particle three dimensional image velocimetry apparatus further comprises an illumination source configured to illuminate at least a portion of said volume within said volume to be imaged.

In still another embodiment, wherein said illumination source is a laser.

In a further embodiment, a plurality of images captured simultaneously is used to derive said velocity fields within said volume to be imaged.

In yet a further embodiment, said data processing apparatus is configured to perform a preprocess step prior to the refocusing step.

According to another aspect, the invention relates to a method of providing synthetic aperture particle three-dimensional (3D) image velocimetry data. The method comprises the steps of: capturing a plurality of images using a plurality of image recording devices, at least two of said plurality of image recording devices oriented so as to view a region of interest along mutually non-parallel directions to generate three dimensional intensity fields; refocusing said plurality of images on at least one refocus planes in the field of view of each image recording device to generate reconstructed three dimensional intensity fields on a plane placed at a location within the imaged volume using a data processing apparatus based on a general purpose programmable computer, said data processing apparatus operating under control of a set of instructions recorded on a machine readable medium; performing intensity field cross-correlation on said reconstructed three dimensional intensity fields to extract velocity fields therefrom; and recording said velocity fields for later use.

In one embodiment, the method further comprises a preprocess step prior to the refocusing step.

In another embodiment, the preprocess step comprises the steps of: subtracting a sliding minimum value having a window size; convolving image data with a 3×3 Gaussian kernel; equalizing histograms to a histogram of said image with the highest contrast; increasing said contrast by trimming a bottom range and a top range of intensity values; and subtracting a sliding minimum value having a window size.

In yet another embodiment said bottom range and said top range of intensity values are 0.1% of said intensity values.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION OF THE INVENTION

Figure 1:
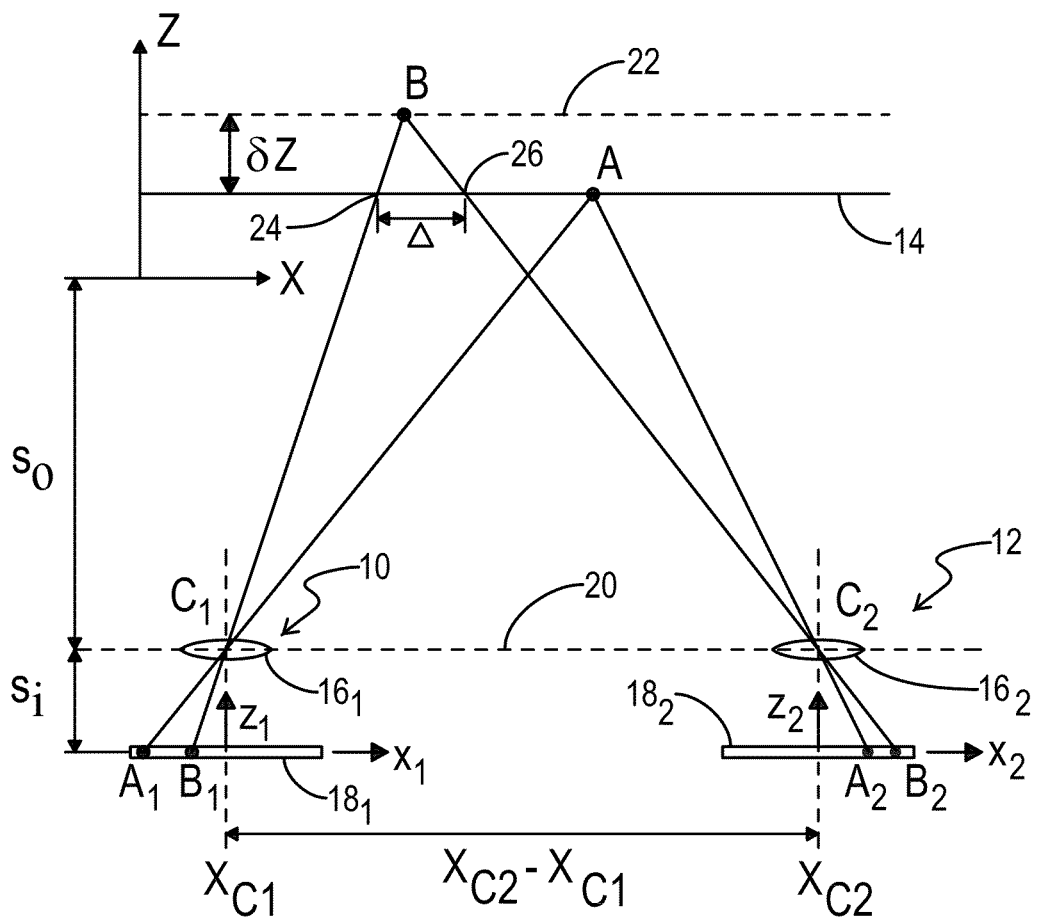
FIG. 1 is a schematic diagram showing the optical arrangement and the concept of parallax in which X-Z is the global coordinate system and x-z are local image coordinates.

We present a new method for resolving three-dimensional (3D) fluid velocity fields using a technique called synthetic aperture particle image velocimetry (SAPIV). By fusing methods from the imaging community pertaining to light field imaging with concepts that drive experimental fluid mechanics, SAPIV overcomes many of the inherent challenges of three dimensional particle image velocimetry (3D PIV). This method offers the ability to digitally refocus a three dimensional flow field at arbitrary focal planes throughout a volume. The viewable out-of-plane dimension (Z) can be on the same order as the viewable in-plane dimensions (X-Y), and these dimensions can be scaled from tens to hundreds of millimeters. Furthermore, digital refocusing provides the ability to "see-through" partial occlusions, enabling measurements in densely seeded volumes. The advantages are achieved using a camera array (typically at least 5 cameras) to image the seeded fluid volume. The theoretical limits on refocused plane spacing and viewable depth are derived and explored as a function of camera optics and spacing of the array. A geometric optics model and simulated PIV images are used to investigate system performance for various camera layouts, measurement volume sizes and seeding density; performance is quantified by the ability to reconstruct the three dimensional intensity field, and resolve three dimensional vector fields in densely seeded simulated flows. SAPIV shows the ability to reconstruct fields with high seeding density and large volume size. Finally, results from an experimental implementation of SAPIV using a low cost 8-camera array to study a vortex ring in a 65×40×32 mm$^3$ volume are presented. The three dimensional particle image velocimetry results are compared with two dimensional particle image velocimetry data to demonstrate the capability of the 3D SAPIV technique.

The technique described herein falls into the multiple-viewpoint category, and makes use of an algorithm known as "synthetic aperture refocusing" to examine the imaged volume. Herein, we focus on the application of the principles of synthetic aperture imaging to develop a measurement system for resolving three-dimensional fluid velocity fields. The system performance is evaluated theoretically and numerically. The practical utility of SAPIV is demonstrated through an experimental study of a canonical vortex ring.

The synthetic aperture PIV technique is implemented using an array of synchronized charge coupled device cameras distributed such that the fields of view overlap. Images are recombined in software using a refocusing algorithm. The result is sharply focused particles in the plane of interest (high intensity), whereas particles out-of-plane appear blurred (low intensity). Due to the multiple camera viewpoints and the effective reduction of signal strength of out-of-plane particles in image recombination, particles that would otherwise be occluded can in fact be seen. The three dimensional intensity field of particle-laden flows can be reconstructed by refocusing throughout the entire volume and thresholding out particles with lower intensities. Typical three dimensional particle image velocimetry techniques can then be applied to the intensity fields to extract velocity data. This technique enables larger volumes to be resolved with greater seeding density, yielding higher spatial resolution than prior three dimensional particle image velocimetry methods. Additionally, the algorithms are simple and robust and build on established image processing techniques. Results of simulated particle fields show the ability to reconstruct three dimensional volumes with seeding densities of 0.17 ppp (6.73 particles/mm$^3$) when the ratio of X-Y to Z dimension is 5:1 (50×50×10 mm$^3$ volume), and 0.05 ppp (1.07 particles/mm$^3$) when the ratio of X-Y to Z dimension is 4:3 (40×40×30 mm$^3$ volume). A vortex ring flow field is imposed on each of these simulated volumes, and three dimensional particle image velocimetry analysis yields highly-resolved vector fields.

Results are presented from an experimental implementation of SAPIV using a custom built camera array to study a vortex ring in a 65×40×32 mm$^3$ volume. Design considerations for experimental 3D SAPIV implementation are discussed throughout the description. The experimental data presented are benchmarked with two dimensional particle image velocimetry, and demonstrate the ability of SAPIV to resolve three dimensional flow fields, providing a useful and flexible tool for making three dimensional particle image velocimetry measurements.

Synthetic aperture PIV is based on the concept of light field imaging, which involves sampling a large number of light rays from a scene to allow for scene reparameterization. In practice, one method used by researchers in the imaging community for sampling a large number of rays is to use a camera array. It is believed that the novelty of the approach presented herein is the application of the reparameterization methods to three dimensional particle image velocimetry, and the development of the technique into a measurement system, including the generation of algorithms to reconstruct three dimensional particle intensity fields from the refocused images. The technique is broken down into sequential components as described below.

Image capture is performed using an array of cameras typically arranged in a multi-baseline stereo configuration, which view the scene from different viewpoints. The cameras can be placed at arbitrary locations and angles as long as the desired refocused planes are in the field of view (FOV) of each camera. The depth of field of each camera is large enough such that the entire volume of interest is in focus. The multiple viewpoints array captures many more light rays than can be seen with one camera (i.e. light field imaging).

In synthetic aperture techniques, images captured by an array of cameras each with large depths of field are post-processed to generate one image with a narrow depth of field on a specific focal plane. Through synthetic aperture refocusing, further post-processing allows the location of the focal plane to be arbitrarily placed within the imaged volume. This technique provides many desirable implications for three dimensional particle image velocimetry; namely, a particle-laden volume can be captured at one instant in time and synthetic aperture refocusing allows for the reconstruction of particles at known depths throughout the volume post capture.

In general, the post-processing for synthetic aperture refocusing involves projecting all images onto a focal surface (planar or otherwise) in the scene on which the geometry is known, averaging the projected images to generate one image, and repeating for an arbitrary number of focal planes. The working principle of the synthetic aperture technique is demonstrated with a simplified example. FIG. 1 provides a diagram of the case where two cameras 10 and 12 view the same portion of a reference plane 14. Each camera has a lens $16_1$ and $16_2$ and a detector $18_1$ and $18_2$. Camera 10 has a lens center of projection $C_1$ which is positioned at X axis location $X_{C1}$, and camera 12 has a lens center of projection $C_2$ which is positioned at X axis location $X_{C2}$. Particles A and B are in an imaged volume within the field of view of cameras 10 and 12. The image from particle A follows rays $A_1$ and $A_2$. The image from particle B follows rays $B_1$ and $B_2$. Detectors or image sensors $18_1$ and $18_2$ are parallel to each other and the camera centers of projection $C_1$ and $C_2$ lie on the same plane 20. The geometric imaging optics are described by four parameters: the focal length (f) of lenses $16_1$ and $16_2$; distances from the lenses $16_1$ and $16_2$ to the front of the imaged volume ($s_o$); distance from lenses $16_1$ and $16_2$ to image plane ($s_i$) and magnification ($M(Z)=-s_i/(s_o+Z)$). Also, the focal length is related to $s_o$ and $s_i$ through the imaging condition: $1/f=1/s_i+1/s_o$.

If the images from each camera are mapped to the reference plane 14, and then all images (now in reference plane coordinates) are averaged, the particle A will be in sharp focus in the averaged image. However, particles at different depths or distances such as particle B on secondary plane 22 will appear out of focus because of the parallax between camera centers of projection $C_1$ and $C_2$. In the average of the reference plane 14 aligned images, the images of particle B from the two cameras will appear at the points 24 and 26 where rays $B_1$ and $B_2$ in FIG. 1 intersect reference plane 14, which are separated by Δ. By adding more cameras, mapping images to the reference plane and averaging, the signal of particle A will grow increasingly larger than that of the off-plane particles.

Figure 2C:
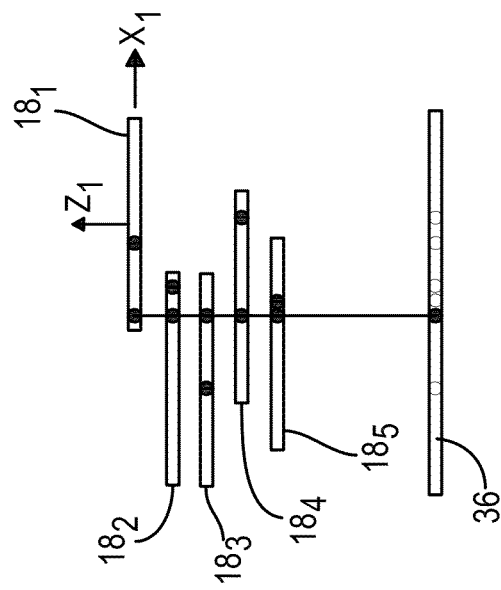
FIG. 2C is a diagram in which multiple images are shifted to align on the plane containing point A, and are averaged to generate a refocused image.
Figure 2B:
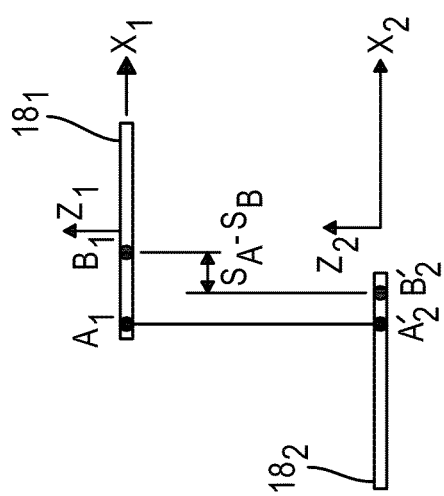
FIG. 2B is a diagram in which the image plane 2 has been shifted to align the images of point A.
Figure 2A:
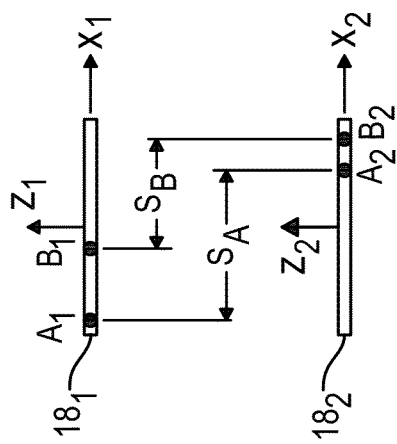
FIG. 2A is a schematic diagram illustrating the synthetic aperture refocusing method in which the z axes of the image planes are aligned.
Figure 2D:
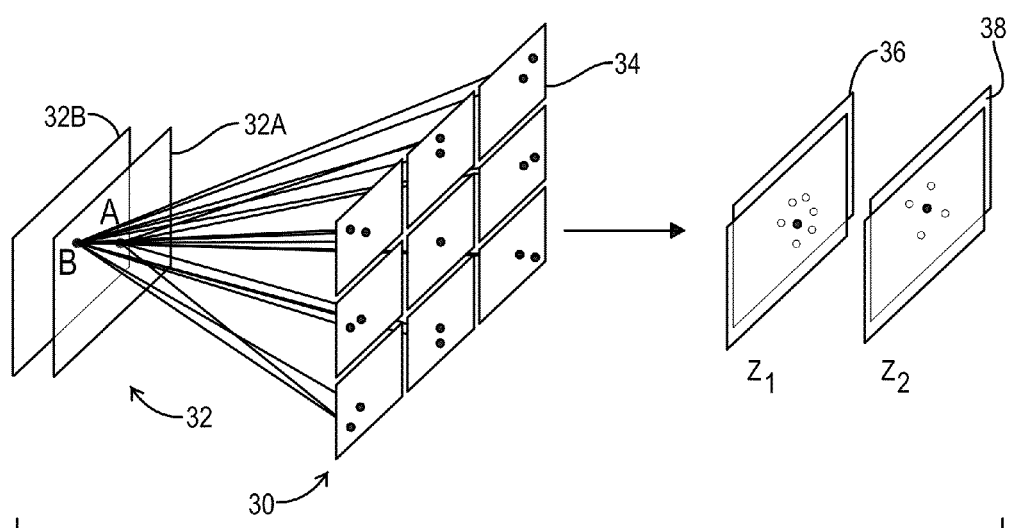
FIG. 2D is a schematic diagram in which is shown a three dimensional depiction of image capture by a 9 camera array, and subsequent refocusing on two planes.

The concept is shown schematically in three dimensions in FIG. 2D, which shows image capture by a nine camera array 30 from a measurement volume 32. Particle A is on plane 32A, and particle B is plane 32B. Planes 32A and 32B are different planes in measurement volume 32. A typical image from a camera is shown at 34. These images are subsequently refocused on two planes 36 and 38. Plane 36 is refocused to the measurement volume 32 plane 32A having particle A, and plane 38 is refocused to the measurement volume 32 plane 32B having particle B. By positioning the cameras on a sufficiently large baseline (larger separation between camera centers of projection), some of the cameras can see particles which are occluded in other images. Therefore, the partially occluded particles retain a high signal in the refocused image.

The goal of the synthetic aperture PIV technique is to reconstruct three dimensional particle intensity fields which are suitable for cross-correlation based three dimensional particle image velocimetry processing. The starting point for volume reconstruction is the implementation of the synthetic aperture algorithm to generate refocused images on planes throughout the volume. Thereafter, the actual particle field must be extracted from the refocused images and organized into a volume with quantifiable locations.

To implement synthetic aperture refocusing, relationships between the image coordinates and focal planes in world coordinates must be established (i.e., a set of mapping functions). In the simulations presented herein, cameras are represented with a pinhole model, and the mapping functions can be generated by an algorithm known in the art. This algorithm is suitable for pinhole cameras with no image distortion and no changes in optical media in the line of sight (e.g. air-glass-water transition). In practice, mapping functions that can account for distortion and changes in optical media can be generated by more sophisticated calibration techniques, as is done for the experiment discussed below. For example, a planar calibration grid can be placed at several planes throughout the volume to generate mapping functions, and error in these functions is reduced using a volume self-calibration technique. The map-shift-average algorithm represents the most basic that is used in synthetic aperture refocusing, but it is helpful in describing the technique and is also implemented in the simulations presented below.

The first step in the map-shift-average algorithm is to align all images on a reference plane. The reference plane is an actual plane in the view of the cameras which, in practice, is defined using a planar calibration grid. Images are aligned on the reference plane by applying a homography which, is a central projection mapping between two planes given by $$bx'=Hx \quad (1A)$$

$$\begin{pmatrix} bx' \\ by' \\ b \end{pmatrix}_i = \begin{bmatrix} h_{11} & h_{12} & h_{13} \\ h_{21} & h_{22} & h_{23} \\ h_{31} & h_{32} & h_{33} \end{bmatrix}_i \begin{pmatrix} x \\ y \\ 1 \end{pmatrix}_i \quad (1B)$$

where b is a constant, $h_{33}=1$, and the vectors x' and x are the homogeneous coordinates of points in the reference plane and the image plane, respectively. In this way the raw image from the ith camera, $I_i$, is mapped to a new image in reference plane coordinates, $I_{RP_i}$. Robust algorithms are known in the art for estimating the homography based on the images of several points on the reference plane.

Light field imaging with camera arrays offers the ability to refocus on arbitrarily shaped focal surfaces. For the simulations herein, we restrict the situation to refocusing on fronto-parallel planes where the raw images are captured with a camera array where all camera centers of projection lie on the same plane. For this restricted case, the mapping that must be applied to refocus on each fronto-parallel plane is simply a shift of the reference-plane aligned images by an amount proportional to the relative camera locations. The coordinates of image points on the new focal plane are given by $$\begin{pmatrix} x'' \\ y'' \\ 1 \end{pmatrix}_i = \begin{bmatrix} 1 & 0 & \mu_k \Delta X_{C_i} \\ 0 & 1 & \mu_k \Delta Y_{C_i} \\ 0 & 0 & 1 \end{bmatrix}_i \begin{pmatrix} x' \\ y' \\ 1 \end{pmatrix}_i \quad (2)$$

where $\mu_k$ is a constant that determines the location of the kth kth focal plane of the refocused image, and $\Delta X_{C_i}$ and $\Delta Y_{C_i}$ are the relative camera locations of the ith camera. This portion of the algorithm transforms the ith reference plane aligned image, to an image on the kth focal plane, $I_{FP_{ki}}$. The relative camera locations can be found using a simple calibration method known in the art which operates on the images from the camera array of points on planes at several depths. No a priori knowledge of the camera locations or optical configurations are required to implement this algorithm.

In the final step in the refocusing algorithm, the mapped and shifted images (now all aligned on the kth focal plane) are averaged. The resultant image is referred to as the refocused image, and is given by $$I_{SA_k} = \frac{1}{N} \sum_{i=1}^{N} I_{FP_{ki}} \quad (3)$$

where images are combined from N cameras. Particles that lie on the plane of the refocused image appear sharp and have high intensity, while particles not on this plane are blurred and have lower intensity. The only difference between the methodology described here and the practical realization comes in the mapping functions used to align all images on the focal planes. Rather than using the linear homography and homology, a higher order mapping is required to deal with distortions and changes in optical media.

Theoretical analysis of the focal plane spacing and viewable depth is presented using the two camera model shown in FIGS. 1, 2A, 2B, 2C and 2D. Here, we define the focal plane spacing, $\delta Z$, as the distance between planes throughout the measurement volume, where Z is the distance from the front of the measurement volume to a given plane. The viewable depth is the total depth dimension ($Z_o$) of the measurement volume. The simple two camera model is sufficiently general to establish the theoretical limits of the system, and the results can be applied to design and predict the performance of various arrangements. A full scale simulated model is implemented hereinafter to examine the effects of parameters not considered in this theoretical treatment, such as particle seeding density, number of cameras and mapping error.

To examine the effect of camera layout on focal plane spacing, we start by considering the relationship between points in physical space and the images of these points. The coordinates of a general point, A (see FIG. 1), projected onto the imaging plane of one of the cameras is given by $$x_A = \left[ \frac{-s_i}{s_o + Z_A} \right](X_A - X_C) - d_C \quad (4)$$

where $X_A$ is the X coordinate of general point A, $Z_A$ is the Z coordinate of general point A, and $X_C$ is the X coordinate of the camera center of projection in global coordinates, and $d_C$ is the displacement of the image sensor from the center of projection (zero as shown). We define the value of "initial" magnification as $M(Z=0)$. The dimension of each pixel projected into physical space is given by $$\delta X = \frac{-p}{M(Z)} \quad (5)$$

where p is the pixel pitch (width of a pixel).

As described earlier, the first step in the reconstruction is to align the images on a reference plane. In FIG. 1, reference plane 14 is chosen (arbitrarily) to be the plane in physical space on which point A lies. In FIG. 2A, the image sensors $18_1$ and $18_2$ are shown with the centers aligned along the z-axes of the local image coordinates. FIG. 2B shows the image sensors $18_1$ and $18_2$ shifted to align the images on reference plane 14. This requires a shift of the image sensor $18_2$ (or equivalently, the digital image) of camera 12 by an amount equal to $s_A = x_{A_2} - x_{A_1}$ (the disparity of the images of point A) in the negative x-direction of the camera 12 coordinate system. Since point B does not lie on the reference plane, $s_B = x_{B_2} - x_{B_1}$ does not equal $s_A$, and thus points at different depths are disambiguated. FIG. 2C shows the shifting and addition of multiple image sensors $18_2$, $18_3$, $18_4$, and $18_5$ to give refocused image 36.

The focal plane spacing, $\delta Z$, is dictated by the image plane shift required to refocus on another plane. To move from the reference plane to the secondary plane shown in the model, the image plane must be shifted by an amount equal to $s_A - s_B$, which is given by $$s_A - s_B = \Delta X_C \left[ \frac{-s_i}{s_o + Z_B} - \frac{-s_i}{s_o + Z_A} \right] \quad (6)$$

where $\Delta X_C = X_{C2} - X_{C1}$ is the separation between the camera centers of projection. The minimum amount that the image sensor can be shifted by is the width of one pixel (assuming no spatial interpolation), therefore $s_A - s_B >= p$. Letting $Z_A = Z$ and $Z_B = Z + \delta Z$ and imposing the minimum shift requirement yields $$\Delta X_C \left[ \frac{-s_i}{(s_o + Z) + \delta Z} - M(Z) \right] = p \quad (7)$$

Solving Equation 7 for $\delta Z$ gives $$\delta Z = -s_i \left[ \frac{\Delta X_C}{p + \Delta X_C \cdot M(Z)} - \frac{1}{M(Z)} \right] \quad (8)$$

Dividing the top and bottom of the first term in the bracket by $1/s_o$ yields $$\delta Z = -s_i \left[ \frac{\left(\frac{\Delta X_C}{s_o}\right)}{\frac{p}{s_o} + \left(\frac{\Delta X_C}{s_o}\right) \cdot M(Z)} - \frac{1}{M(Z)} \right] \quad (9)$$

Equation 9 contains the convenient geometric parameter, $$\frac{\Delta X_C}{s_o},$$

which is the ratio of the camera spacing to the distance from the front of the imaged volume. For convenience, we will let $$D \equiv \frac{\Delta X_C}{s_o}.$$

This parameter characterizes the baseline of the system. Equation 9 can be further simplified by applying Equation 5 at Z to replace p and rearranging, $$\frac{\delta Z}{\delta X} = \frac{\frac{1}{D} + \frac{Z}{Ds_o}}{1 - \frac{\delta X}{Ds_o}} \quad (10)$$

For typical PIV applications, it is reasonable to assume $\delta X = Ds_o$; applying this approximation yields $$\frac{\delta Z}{\delta X} \cong \frac{1}{D} + \frac{Z}{Ds_o} \quad (11)$$

Therefore, the ratio $\delta Z/\delta X$ is a linear function of Z with intercept defined by the camera baseline and slope defined by the camera baseline and the imaging system optics. The depth of field in the reconstructed volume is directly related to $\delta Z/\delta X$. When $\delta Z/\delta X$ is small, the camera lines of sight are at large angles to one another, and the physical depth over which particles are in focus is small (small depth of field). Conversely, larger $\delta Z/\delta X$ leads to a larger depth of field, which is manifested as reconstructed particles which are elongated in Z.

In theory, the overall viewable range in X, Y and Z is limited only by the field of view (FOV) and depth of field (DOF) of a single camera of the array. In reality, images from the outer cameras of the array must be shifted with respect to the central camera image to refocus at different depths. The outer edges of the refocused images have a lower signal-to-noise ratio than regions where all images contribute to the average. This effective limitation on the field of view can be characterized by the number of image shifts required to refocus through an entire volume, which is given by $$N = \frac{Z_o}{\delta Z} \quad (12)$$

where $Z_o$ is the depth of the volume. Since images are shifted in integer pixel increments (assuming no interpolation), it is possible to calculate the region of each refocused image to which all images will contribute. As will be seen hereinafter, this effect does degrade the performance near the outer edges of the larger reconstructed volumes. This effect could be mitigated by excluding the portions of the shifted images which don't contribute from the average. Nonetheless, the implications of the technique are that the observable range of the system is highly scalable, with the ability to trade-off depth of field for viewable range much as one would trade-off X-Y resolution for field of view with a single camera.

Figure 3A:
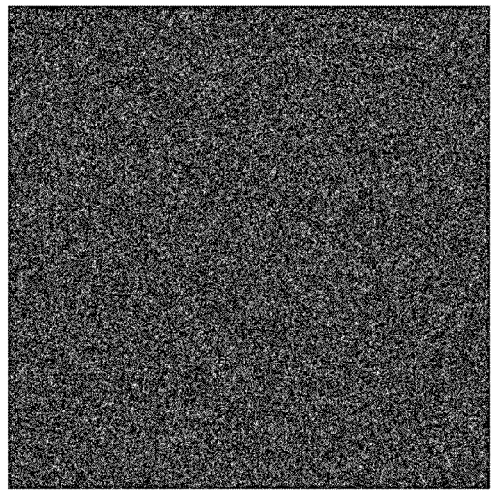
FIG. 3A is a diagram showing a simulated image from the central camera of the array.
Figure 3B:
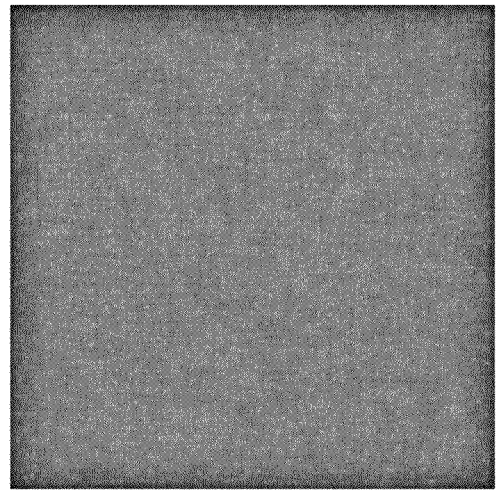
FIG. 3B is a zoomed view diagram showing a refocused image using all of the simulated images of the array.
Figure 5:
FIG. 5 is a zoomed view diagram of the thresholded refocused image from FIG. 3B revealing the particles and removing the background noise.
Figure 4A:
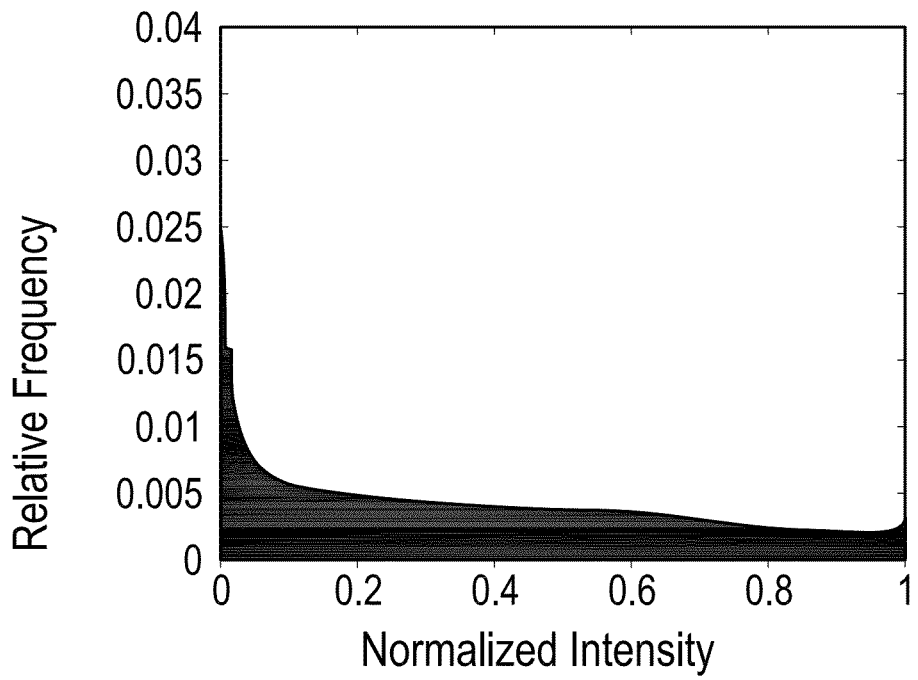
FIG. 4A is an intensity histogram for a single simulated image aligned on a given focal plane.
Figure 4B:
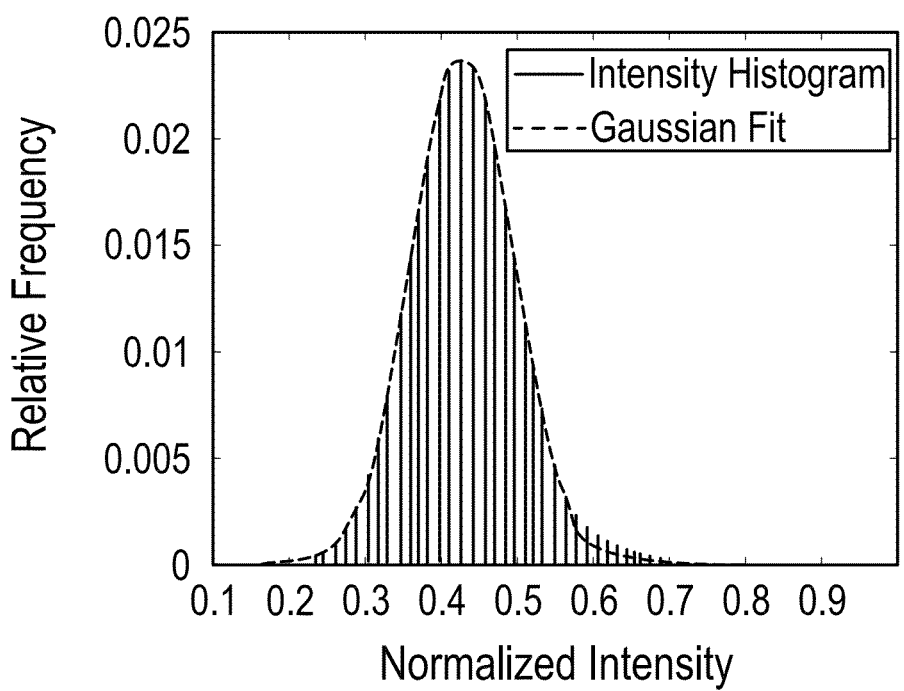
FIG. 4B is an intensity histogram for a refocused image on that given focal plane.

Once the refocused images have been generated, the images must be processed to extract the particles in the plane of interest from the blurred, lower intensity background. (The blurred lower intensity background represents particles on other planes.) FIG. 3A shows a zoomed view (250×250 pixels) of simulated image from the central camera of the array and FIG. 3B shows a refocused image from the 50×50×10 mm³ volume simulation which will be described in detail hereinafter. The refocused image has a higher background "noise" level than the raw image or a typical two dimensional particle image velocimetry image due to the averaging of multiple images, however the "noise" is probabilistic. If we consider the intensity fields of the N images aligned on a given focal plane to be independent and identically distributed random variables, $I_1, I_2, \ldots, I_N$, with means $\mu$ and standard deviations $\sigma$, then the central limit theorem states that the distribution of the average of the random variables will be Gaussian with mean $\mu$ and standard deviation of $\sigma/\sqrt{N}$. Therefore, the intensity distribution of a refocused image (which is an average of the focal plane aligned images) can be modeled as Gaussian. FIG. 4A shows the intensity histogram for a reference plane-aligned image from one camera of the array and the histogram for the refocused image in FIG. 3B is shown in FIG. 4B. Clearly, the distribution of intensity for the single camera image is not Gaussian, but the shape of the distribution of the refocused image follows a Gaussian distribution quite well, as indicated by the model fit. As more particles are added, the mean of the individual images becomes larger, and thus the mean of the refocused image becomes larger. Plane of interest particles appear with high intensity values, and are thus outliers with respect to the distribution of the refocused image. Intensity thresholding can be applied to retain plane of interest particles and eliminate background "noise" caused by other planes from the images. It was found that a threshold value around three standard deviations above the mean intensity of each refocused image yielded acceptable reconstruction. FIG. 5 shows the refocused image from FIG. 3B now thresholded to reveal the particles in the plane of interest. By refocusing throughout the volume and thresholding the refocused images, the three-dimensional intensity field is reconstructed. By detecting the outliers in the refocused images, the true particle plane of interest can be reconstructed, attesting to the simplicity of the SAPIV technique.

A 5×5 camera array model is simulated to investigate the system performance as a function of particle seeding density, size of measurement volume and error in the mapping function. The effect of array layout and camera number on reconstruction performance is also investigated by changing the spacing between cameras and removing certain cameras from the array, respectively. Cameras are arranged with centers of projection on the same plane and equal spacing along X and Y between all camera centers of projection (unless otherwise noted). In order to overlap the fields of view, the cameras are angled such that the ray passing through the center of the measurement volume intersects the center of the image sensor. For this arrangement, the map-shift-average algorithm applies. The perspective due to the angling of the cameras is compensated for when the reference plane homographies are applied to the images.

The ability of the system to resolve the particle field in four different measurement volume sizes is examined. The volume sizes (X×Y×Z) are 50×50×10 mm³, 40×40×30 mm³, 50×50×50 mm³ and 100×100×100 mm³. For each volume, the system performance is evaluated for several different camera baselines, D, and for each camera baseline the particle seeding density is varied. For all simulations presented herein, the cameras are modeled with 85 mm focal length lenses and the imaging sensors are 1000 pixels×1000 pixels with a pixel pitch of 10 μm. For the 100×100×100 mm³ volume, the initial magnification is set to M (Z=0)=−0.1 and for the other three volumes the magnification is M (Z=0)=−0.2.

Reference plane homographies are calculated for each camera from calibration images of known points on several Z planes with the central camera of the array as the reference camera. The camera positions relative to the central camera are established using a calibration method known in the art. The calibration images are used to establish the shift required to refocus at each depth in order to define the conversion between voxels and physical units in the Z dimension. Herein, we define a voxel as having the dimensions of a pixel in X and Y, and dimension equal to the focal plane spacing in Z. Because integer pixel shifts are used in the map-shift-average algorithm, a given calibration depth may not correspond exactly to any of the refocused images. Therefore, the actual voxel to Z calibration is approximated by fitting a gaussian curve to the summed intensity from refocused images surrounding each calibration plane and finding the voxel corresponding to the peak of the fit.

Particles are randomly seeded within the volume and imaged using the camera array. Once the image plane coordinates of a point are known, a realistic model of the intensity distribution must be applied. A standard method of simulated image generation is to apply a Gaussian intensity profile. The distribution is applied to each camera image for each pixel location, which forms an image similar to the one presented in FIG. 3A.

After simulated images have been formed by each camera, the map-shift-average algorithm, followed by intensity thresholding and three-dimensional field reconstruction, is carried out for each numerical experiment. In order to quantify how well the intensity field is reconstructed, a known measure of reconstruction quality, Q, is applied here:

$$Q = \frac{\sum_{X,Y,Z} E_r(X, Y, Z) \cdot E_s(X, Y, Z)}{\sqrt{\sum_{X,Y,Z} E_r^2(X, Y, Z) \cdot \sum_{X,Y,Z} E_s^2(X, Y, Z)}} \quad (13)$$

where $E_r$ is the reconstructed intensity field and $E_s$ is a synthesized intensity volume based on the known particle locations.

Baseline spacing affects the Z dimension of the voxels such that they represent larger physical sizes than the X-Y dimensions, therefore the intensity distribution in the synthesized field is scaled in Z in voxel space such that in physical space the intensity distribution is spherically symmetric. This ensures that a perfectly reconstructed particle would yield a Q value of 1 when compared to the synthesized field.

Figure 6A:
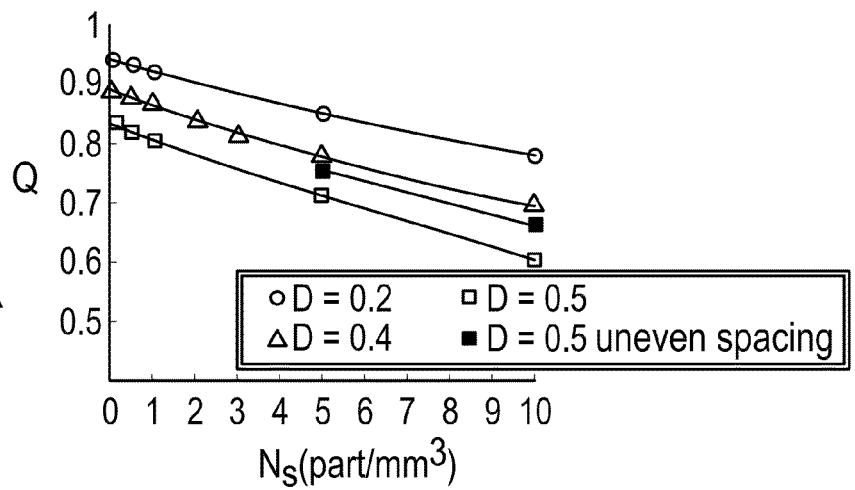
FIG. 6A is a diagram showing the effect of particle seeding density (C, particles/(mm)$^3$) on reconstruction quality, Q, for various camera baselines for a 50×50×10 mm$^3$ volume.
Figure 6B:
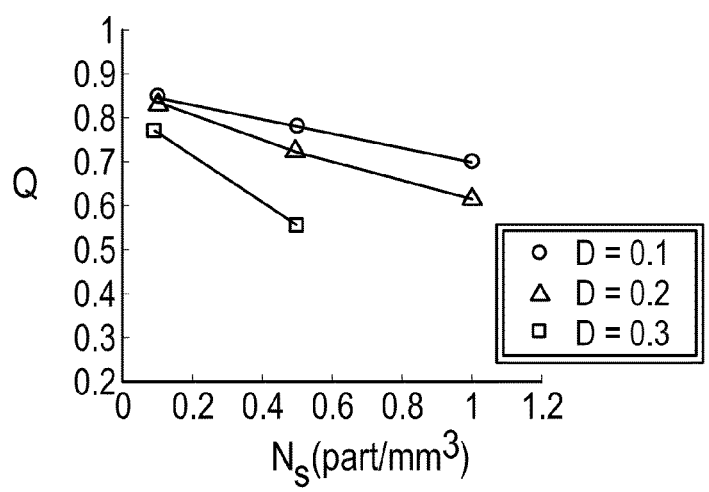
FIG. 6B is a diagram showing the effect of particle seeding density (C, particles/(mm)$^3$) on reconstruction quality, Q, for various camera baselines for a 50×50×50 mm$^3$ volume.
Figure 6C:
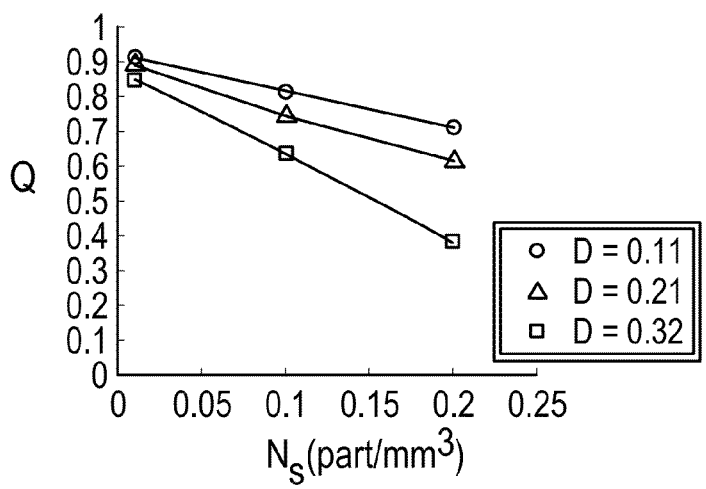
FIG. 6C is a diagram showing the effect of particle seeding density (C, particles/(mm)$^3$) on reconstruction quality, Q, for various camera baselines for a 100×100×100 mm$^3$ volume.

The value of Q is calculated for each numerical experiment conducted, and we use the requirement of Q≥0.75 for the reconstruction to be considered adequate. In all cases other than the 40×40×30 mm³ measurement volume, the outer 50 edge pixels were cropped prior to calculating Q because of the effective loss in field of view as described earlier (in the 40×40×30 mm³, the images do not fill the entire image sensor and thus the outer pixels of the reconstructed images contain no particles). FIGS. 6A, 6B and 6C present the reconstruction quality as a function of particle seeding density for various camera baselines in each volume. The number of seeded particles, maximum particle seeding density (C) and number of particles per pixel (ppp) in each case are summarized in Table 1. To find the maximum seeding density, simple linear interpolation of the data was used to find the seeding density corresponding to Q=0.75.

TABLE 1

| Measurement Volume (mm³) | D | δX | δZ/δX | C (part./mm³) | Part./pixel (ppp) | # part. |
|---|---|---|---|---|---|---|
| 50 × 50 × 10 | 0.2 | 0.05 | 5.00 | >10 | >0.25 | >250000 |
|  | 0.4 | 0.05 | 2.5 | 6.73 | 0.17 | 168150 |
|  | 0.5 | 0.05 | 2 | 3.34 | 0.08 | 83464 |
|  | 0.5 (uneven) | 0.05 | 2.00 | 5.29 | 0.13 | 132230 |
| 40 × 40 × 30 | 0.4 (uneven) | 0.05 | 2.51 | 1.07 | 0.05 | 51179 |
| 50 × 50 × 50 | 0.1 | 0.05 | 10.24 | 0.70 | 0.09 | 87573 |
|  | 0.2 | 0.05 | 5.13 | 0.42 | 0.05 | 52072 |
|  | 0.4 | 0.05 | 2.56 | 0.14 | 0.02 | 17282 |
| 100 × 100 × 100 | 0.11 | 0.1 | 9.40 | 0.16 | 0.16 | 164200 |
|  | 0.21 | 0.1 | 4.70 | 0.10 | 0.10 | 96149 |
|  | 0.32 | 0.1 | 3.13 | 0.05 | 0.05 | 51854 |

In the case of the 50×50×10 mm³ measurement volume, the reconstruction quality falls off with increasing seeding density, and also decreases with increasing camera baselines. For larger seeding density, the reduction in reconstruction quality is expected; the occurrence of off-plane particle overlap is increased, and the overall signal-to-noise ratio decreases in the refocused images. The reason for reduced reconstruction quality with increasing baseline is less obvious. Investigation of the data reveals that the reason for the degradation in reconstruction quality with increasing baseline is due to the more extreme warping of the particle images imposed by the homography which maps images to the reference plane. The particles become elongated in the mapped image which raises the background noise in the refocused images. This may be mitigated by placing the outer cameras of the array a normalized distance D/2 from the inner cameras (which determine the focal plane spacing of the system and would still be placed a normalized distance D from the central camera) but requires interpolation when shifting images from the outer cameras of the array. This has been implemented in the case labeled D=0.5 uneven spacing, and indeed the reconstruction quality is improved for the same seeding density. For this configuration, the achievable seeding density is C=5.29 part./mm³ and the resultant particles per pixel is 0.13.

Simulations in the 50×50×50 mm³ volume show a similar trend as for the 50×50×10 mm³ volume, with Q decreasing with increasing C more rapidly for a larger camera baseline. However, the achievable seeding density is lower than for the volume with smaller depth (e.g. C=0.4 part./mm³ for D=0.2). The reasons for the lower seeding density and the lower actual number of particles that can be seeded as compared to the 50×50×10 mm³ volume are four-fold. First, the larger depth of field of each camera requires a larger f-number which increases the particle image diameter. This results in a larger mean intensity in the refocused image. Second, the depth of the volume creates more likelihood of particle overlap on each simulated image, which can, in a sense, decrease the dynamic range of the system by increasing the likelihood of saturated pixels. Third, the larger depth creates a higher likelihood of overlapping of many different out-of-focus particles in the refocused images. These false particles may be retained in the thresholding if enough images overlap. Finally, the limitation on the field of view imposed by the image shift contributes to the loss in reconstruction quality because some images contribute zero values to the average toward the outer regions of the refocused images, thus particles in the plane of interest have a lower intensity value. This can be mitigated by averaging only the portions of the image which are known to contribute to the refocused image, but that technique has not been implemented here. Tuning the camera array and reconstruction algorithms to enable more seeding in the very large volumes is the subject of ongoing work. By decreasing the dimensions of the volume somewhat, more particles can be seeded, even in volumes where the Z dimension approaches that of the X-Y dimensions, and all are relatively large. Simulations in the 40×40×30 mm³ volume are carried out at only one array configuration—D=0.4 uneven spacing—and it was found that a seeding density of C=1.07 part./mm³ corresponding to 0.05 particles per pixel could be achieved. As shown the Section titled Synthetic three dimensional Flow Fields, this seeding density allows three dimensional particle image velocimetry measurements to be made in this volume with reasonable spatial resolution.

Finally, the camera magnifications are reduced to accommodate the large 100×100×100 mm³ measurement volume. The trend for reconstruction quality as a function of seeding density and baseline is similar to that observed for the other volumes studied. The total number of particles that can be seeded is, however, larger than for the 50×50×50 mm³ volume for comparable camera baselines. Thus, trading off X-Y resolution allows for more particles to be seeded even with increasing depth dimension. Overall, these results indicate that the synthetic aperture PIV technique is capable of imaging extremely densely seeded volumes where the depth dimension is somewhat reduced, and still quite densely seeded volumes when the Z dimension approaches that of the X-Y dimensions.

Figure 7:
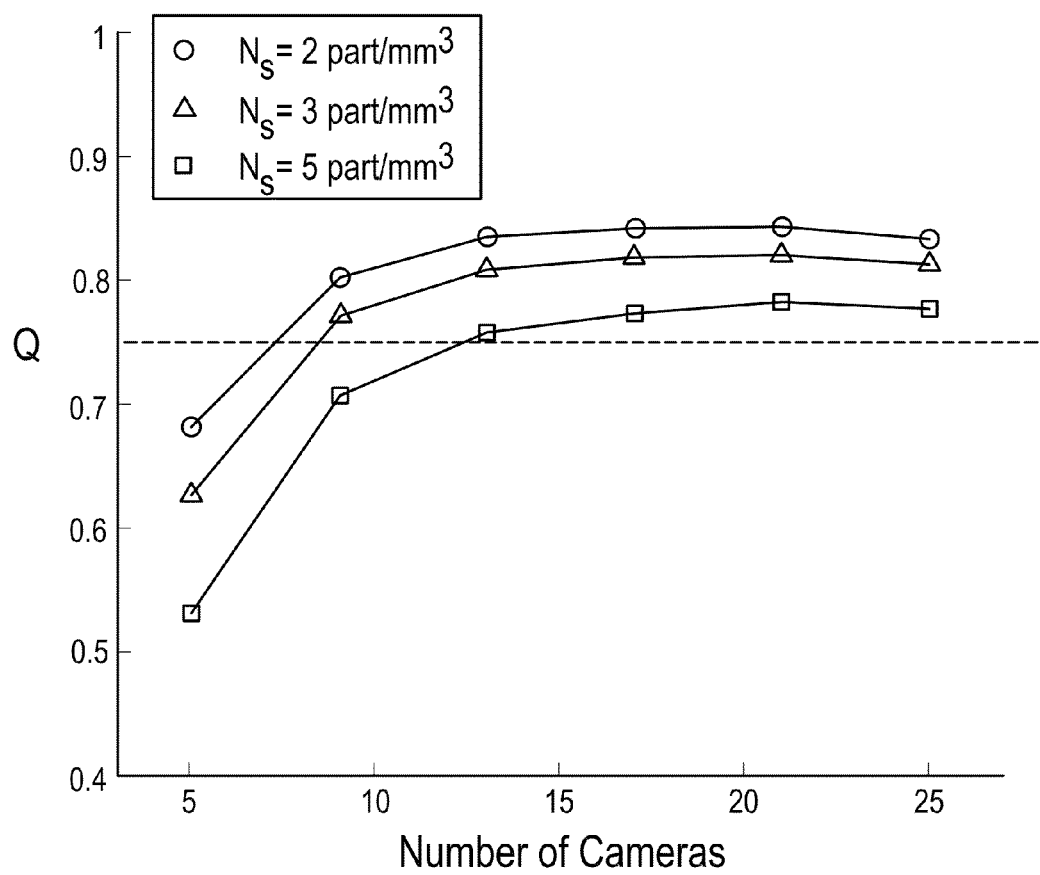
FIG. 7 is a graph illustrating the Reconstruction quality, Q, as a function of camera number for various particle seeding densities in the volume.

The effect of camera number on reconstruction quality is investigated in the 50×50×10 mm³ volume by using only some of the cameras in the array. FIG. 7 shows Q as a function of camera number with seeding densities of 2, 3 and 5 part./mm³. Clearly, the reconstruction quality reaches a point of diminishing returns as more cameras are added, and the most efficient number of cameras seems to be in the range of 10-15.

Two synthetic flow fields are simulated to assess the ability of the synthetic aperture PIV method in reconstructing three dimensional intensity fields that are suitable for cross-correlation based three dimensional particle image velocimetry analysis. In each simulation, the fluid motion is prescribed by the same equation for a vortex ring as known in the art, where the velocity magnitude is given by $$|V| = \frac{8KR}{l} e^{-\frac{R}{l}} \quad (14)$$

where R is the radial distance of a point from the toroidal axis of the vortex ring and l is a length scale determining the size of the vortex ring (chosen to be 4 mm). The constant, K, is a conversion factor from voxel to physical units and is required since, in the present case, the synthetic particles are seeded in physical space and imaged by the model camera array. The toroidal axis forms a circle of diameter 20 mm. The first synthetic experiment is carried out in a 50×50×10 mm³ volume where the central axis of the toroid is parallel to the Z-axis. The volume is seeded with 125,000 particles (C=5 part/mm³), and images are simulated in a 21 camera array with spacing D=0.5 (uneven spacing, see Table 1) and magnification M (Z=0)=−0.2. This results in a reconstruction quality of Q=0.76. The maximum displacement in this flow field is 0.3 mm which corresponds to 6 voxels in X and Y and 2.9 voxels in Z.

Since the reconstructed volumes are intensity fields, a cross-correlation based PIV calculation is suitable for calculating vector fields. Many different cross-correlation techniques are know in the art. In the present study, we have adapted an open-source two dimensional particle image velocimetry code, matPIV, for three dimensional functionality. Other PIV calculation programs could be used for this purpose. A multipass algorithm with a final interrogation volume containing 32×32×16 voxels and 75% overlap generates 327448 vectors (122×122×22 vectors). The Z dimension of the interrogation volumes in voxel units is half that of the X-Y dimension because the focal plane spacing is twice the pixel size for this camera configuration. Each interrogation volume contains approximately 20 particles, based on the gross particle seeding density.

Figure 8A:
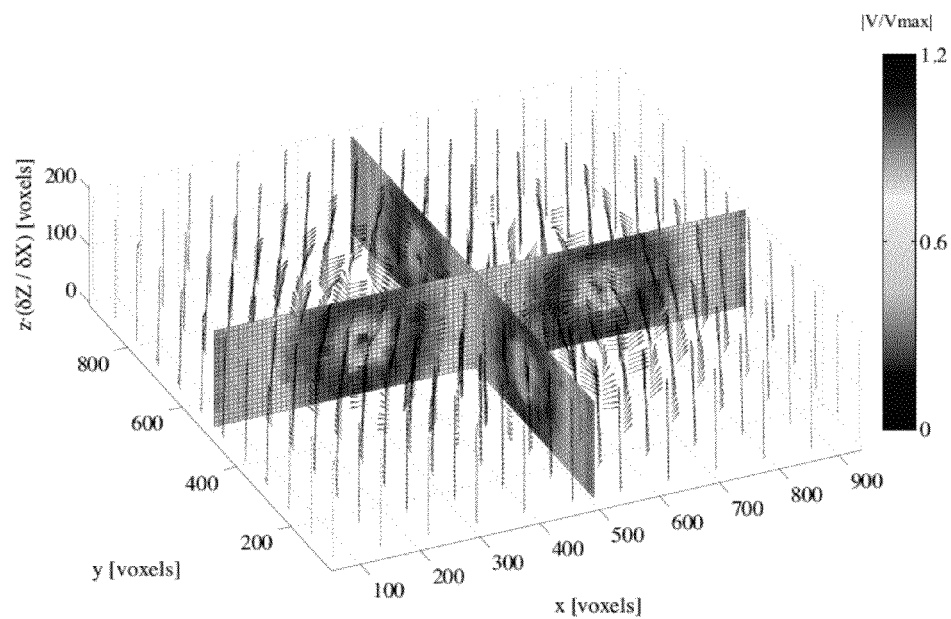
FIG. 8A is a diagram illustrating the three-dimensional vector field resulting from PIV processing of the reconstructed intensity volumes using SAPIV in the 50×50×10 mm$^3$ volume that shows two cuts with normalized velocity magnitude contours.
Figure 8B:
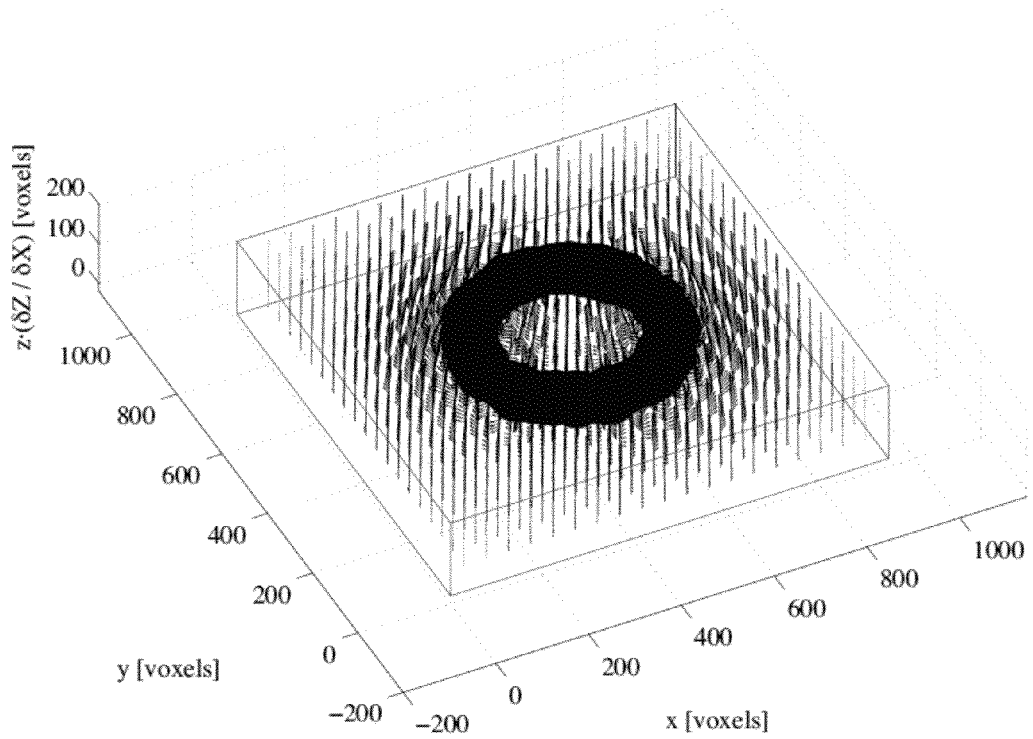
FIG. 8B is a diagram illustrating the three-dimensional vector field resulting from PIV processing of the reconstructed intensity volumes using SAPIV in the 50×50×10 mm$^3$ volume that shows the vector field and a vorticity iso-surface (0.15 voxels/voxel).

FIG. 8A shows the resultant velocity field with every tenth vector plotted in X and Y and every vector plotted in Z. The Z voxel and velocity values are multiplied by $$\frac{\delta Z}{\delta X}$$

to create the correct aspect ratio for plotting purposes. The fields are plotted in voxel units; if converted to physical units, the data set would not be cubical. Two slices are shown with normalized velocity magnitude contours revealing the vortex ring structure and symmetry. The maximum velocity magnitude in the exact known field is used to normalize the velocity magnitude in the processed field. FIG. 8B shows the vector field and a vorticity iso-surface (0.15 voxels/voxel) with every fourth vector plotted in X and Y and every vector plotted in Z.

To quantitatively evaluate the performance, both the reconstructed three dimensional intensity fields and the synthesized three dimensional intensity fields are processed using the three dimensional adaptation of matPIV, and each is compared to the exact velocity field. The error is defined as the difference between the processed and exact field at every vector location. By comparing the PIV results for both fields, error due to the PIV algorithm itself can be identified. Both the synthesized and reconstructed volumes are processed using exactly the same window sizes, PIV code and filtering routines. We will refer to the vector fields resulting from PIV processing of the reconstructed three dimensional intensity fields and the synthetic three dimensional intensity fields as the reconstructed vector field, and synthesized vector field, respectively.

Error can be computed for each vector component for the reconstructed vector field. This calculation indicates that most of the error is due to the PIV algorithm itself, and a much smaller percentage is due to the actual intensity field reconstruction. This is not surprising since the three dimensional particle image velocimetry algorithm is not very sophisticated, and we would expect a reduction in error magnitude with a more advanced three dimensional particle image velocimetry algorithm.

In the second simulated flow, a vortex ring of the same size is oriented with the central axis of the toroid parallel to the X-axis, such that the ring spans deeper into the flow in the Z dimension. The 5×5 model camera array is used with spacing D=0.4 (uneven spacing, see Table 1) and the magnification is set to M(Z=0)=−02. The maximum displacement in the flow field is 0.37 mm which corresponds to 7.3 voxels in X and Y and 2.9 voxels in Z. A particle seeding density of C=1 part/(mm)$^3$ in a 40×40×30 mm$^3$ volume results in a distribution of 48,000 particles (resulting in Q=0.75). The lower seeding density requires larger interrogation volume sizes in order to contain an appropriate number of particles, therefore a final interrogation volume containing 60×60×24 voxels is used with each containing 27 particles based on the seeding density. Using 50% overlap in the multipass three dimensional particle image velocimetry calculation yields 18,432 vectors (32×32×18), which includes the imaged area that contained no seeding particles (with a magnification of −0.2, images of the seeded volume did not span the entire imaging sensor).

Figure 9:
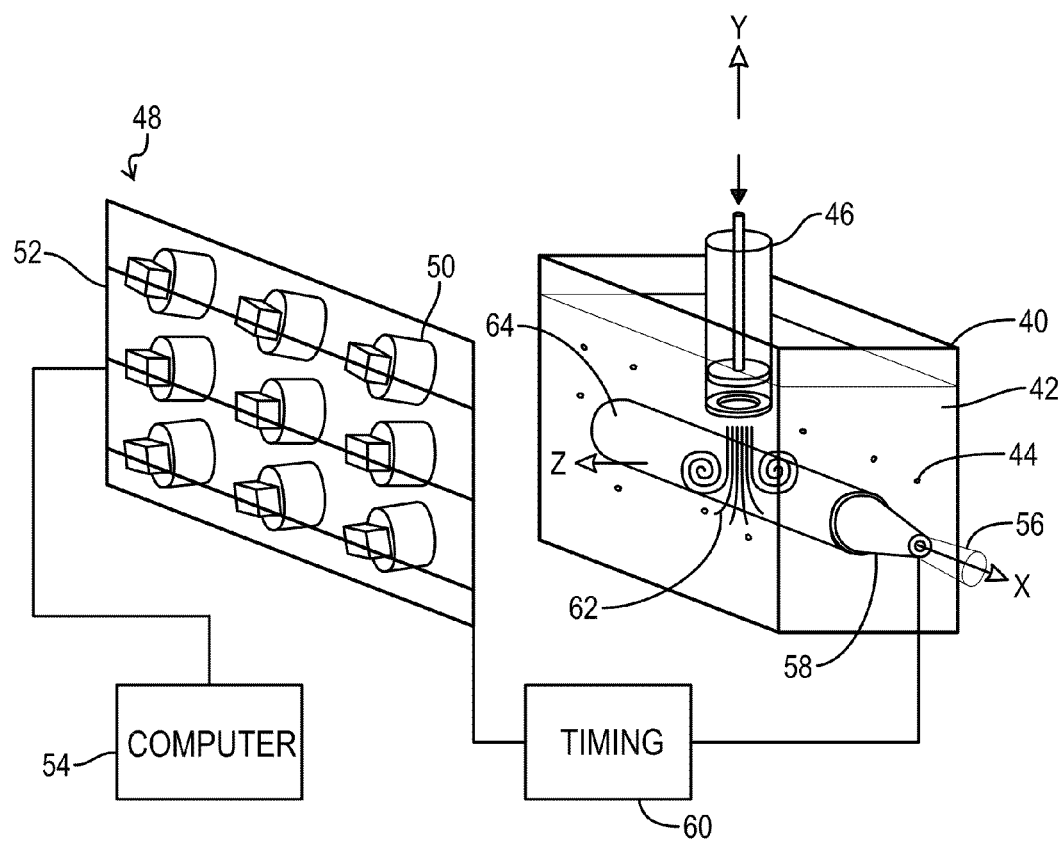
FIG. 9 is a diagram illustrating the experimental setup in which a camera array images a vortex ring illuminated with a laser.

To illustrate the capabilities of the SAPIV technique in practice, a canonical three dimensional flow field is captured experimentally using an array of eight cameras. Instantaneous 3D-3C SAPIV and classic two dimensional particle image velocimetry velocity data of a piston-generated vortex ring are acquired for comparison. A diagram of the experimental setup is given in FIG. 9.

The experiment is conducted in a glass tank 40 filled with fluid 42 and seeded with neutrally buoyant particles 44. A cylindrical piston-driven vortex ring generator 46 is mounted in the center of the tank 40. In this embodiment water was used as fluid 42. A camera array 48 is oriented to image tank 40 from the side. Camera array 48 has nine cameras 50 mounted on a common frame 52. Cameras 50 are angled in order to overlap the fields of view. As shown previously, reconstruction quality reaches a point of diminishing returns as more cameras 50 are added, and that the most efficient number of cameras is in the range of 10-15, as shown in FIG. 7.

In this embodiment, cameras 50 in array 48 are capable of capturing 1024×768 pixels, 8 bit, monochromatic images at 10 frames per second. The cameras are connected to a single computer 54 which records the data. Classic PIV frame straddling timing is used to obtain appropriate image pair time spacing. A pulsed laser 56 joined to a beam expander 58 is used to illuminate the particle volume. A timing box 60 synchronizes the cameras 50 and laser 56.

In use, piston 46 produces a vortex ring 62 in fluid 42. Vortex ring 62 causes movement of particles 44. Particles 44 are illuminated at intervals by beam 64 from beam expander 58. Simultaneously, as triggered by timing box 60, Camera array 48 records images from illuminated particles 44. Recorded images are provided to computer 54 for processing.

To achieve proper focus in synthetic aperture images, accurate mapping between image and world coordinates is required. The mapping is found by imaging a precision machined calibration plate traversed through the target volume with Z location increments of 2 mm. Since the SAPIV technique involves reprojecting the images onto several planes throughout the volume, a suitable coordinate system must be established on the calibration plate. Here, we use the average calibration in pixels/mm from the center camera image of the plate at the Z location farthest from the cameras to convert the reference geometry of the calibration plate from mm to pixels. Second-order polynomial fits are used to map image coordinates to reference coordinates on each Z calibration plane, and linear interpolation is used to find the polynomial fits on Z planes between each calibration plane. This approach follows that of prior Tomographic-PIV studies where polynomial fits are used to deal with the distortion introduced when imaging through an air-glass-water transition. The error in the mapping functions should be less than 0.45 pixels for adequate reconstruction in SAPIV. Volume self-calibration is not implemented in the present experiment, yet reconstruction still yields a volume which is suitable for three dimensional particle image velocimetry. Implementing volume self-calibration will improve greatly the particle yield rate in the reconstruction.

The synthetic aperture images are formed with focal plane spacing of 0.2 mm in Z. Theoretically, the number of focal planes that can be generated within an illuminated volume is infinite, but the information on each plane will not necessarily be unique, as the sharpness of a refocused object is determined by the degree to which mapped images of the object overlap. For example, it is possible to generate focal planes very close to each other by shifting all images by a very small amount. However, if the shift size is much smaller than the refocused object, the two refocused images will be essentially indistinguishable, in which case the information is redundant. Therefore, focal plane spacing (which determines voxel size) should be made large enough so as not to retain redundant information. The depth over which objects are in focus can be controlled by changing the camera baseline, D; for the present experiment, D=0.2. Ultimately, smaller focal plane spacing should yield better resolution in the Z dimension of the reconstructed fields, and thus the vector fields. The influence of focal plane spacing and camera baseline on the accuracy and resolution of three dimensional particle image velocimetry vector fields is the subject of ongoing work.

Other volumetric PIV studies have discussed the need for image preprocessing to deal with non-uniformities in laser profiles and pulse intensities, as well as to remove background noise. Prior to refocusing, images are subjected preprocessing. A sliding minimum was subtracted from the images with a window size of 10 pixels. The image was convolved with a 3×3 Gaussian kernel. The histograms of the images were equalized to the histogram of the image with the highest contrast. The contrast of each image was increased by trimming the bottom and top 0.1% of intensity values. Finally the step of subtracting a sliding minimum was conducted again.

Figures 10A, 10B, 10C:
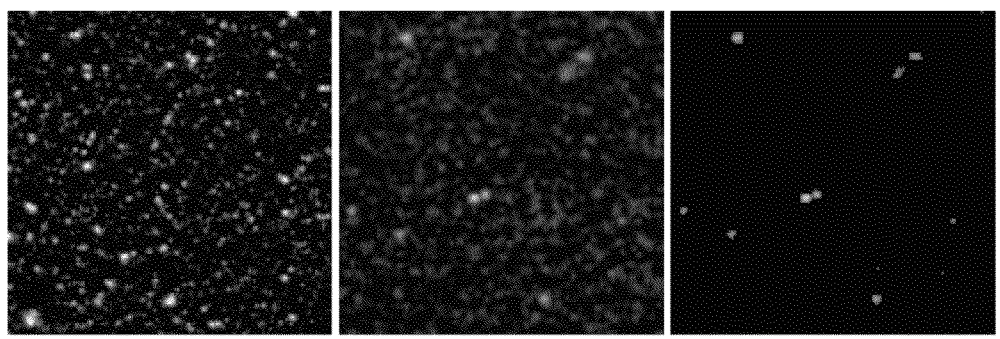
FIG. 10A illustrates a zoomed view of a preprocessed three dimensional particle image velocimetry image from single camera of the array.
FIG. 10B illustrates a refocused image at Z=5 mm.
FIG. 10C illustrates a thresholded image at Z=5 mm.

After preprocessing, the images are mapped to each plane throughout the volume, averaged to form the synthetic refocused image, and thresholded to retain particles to generate an intensity volume for each time instant. Because the mapping functions are not simple linear homographies, interpolation is required to re-project the images; here, a bilinear interpolation is used. FIG. 10A shows a preprocessed image from the array. FIG. 10B shows a synthetic aperture refocused image at one depth. FIG. 10C shows a thresholded image at the same depth.

Once reconstructed, the intensity volumes are ready for cross-correlation based three dimensional particle image velocimetry analysis; the adapted version of matPIV is again employed. A multi-pass algorithm with one pass at an initial interrogation volume size of 128×128×64 voxels and two passes at an final interrogation volume size of 64×64×32 voxels and 50% overlap generates a 23×31×11 vector field. Each 64×64×32 voxels interrogation volume contains approximately 15 particles. The resultant vector field resolution is 2.1 mm in X and Y and 3.2 mm in Z. Post-processing consists of a filter based on signal-to-noise ratio of the cross-correlation peak, a global filter which removes vectors five standard deviations above the mean of all vectors, and a local filter which removes vectors which deviate by more than three standard deviations from the median of a 3×3×3 vector window. The filtered field is interpolated using linear interpolation and smoothed with a 3×3×3 gaussian filter. At this point some mention should be made of the overall processing time. The time required to reconstruct the two volumes used to generate the three dimensional vector field is 18% of the time required for the three dimensional particle image velocimetry processing of the fields. Therefore, the limiting time factor in processing is the three dimensional particle image velocimetry analysis, which demonstrates the relative efficiency of the synthetic aperture refocusing technique.

Figure 11A:
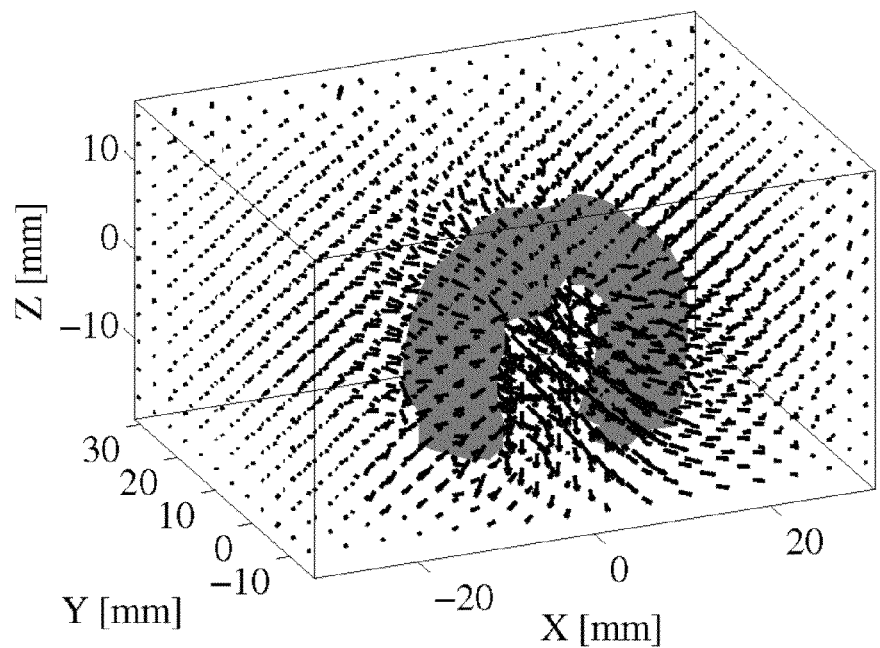
FIG. 11A illustrates an experimental SAPIV velocity vector field for the vortex ring with an iso-vorticity contour of magnitude 9 s$^{-1}$, with superimposed velocity vectors.
Figure 11B:
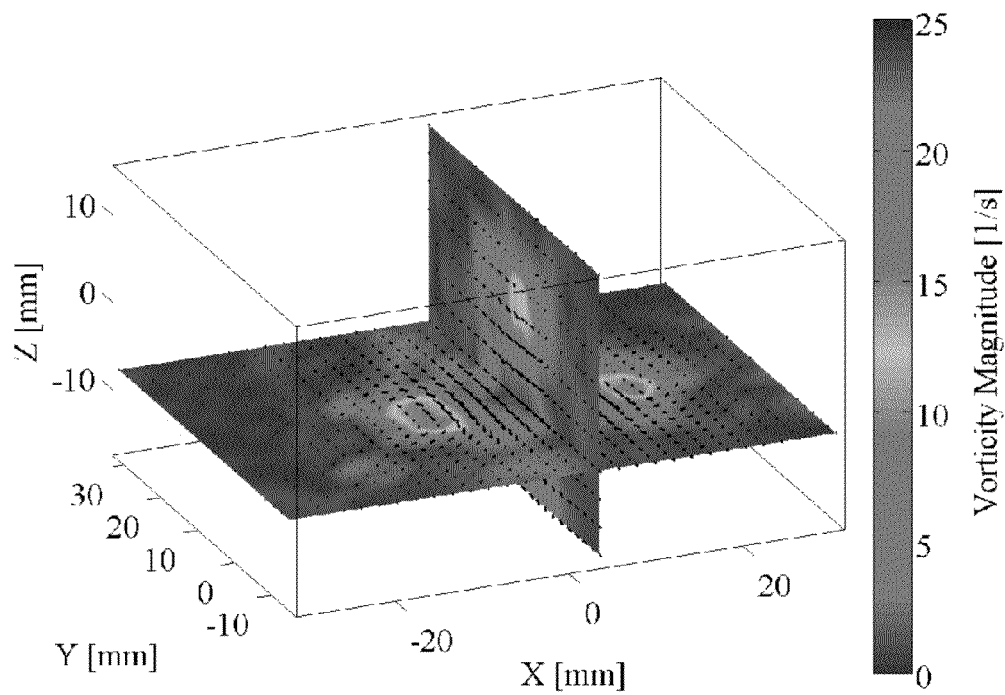
FIG. 11B illustrates X-Y and Y-Z cross-sectional cuts of vorticity through the vortex ring center.

Experimental results for the instantaneous three dimensional velocity data of the vortex ring are shown in FIG. 11A; the resultant three dimensional vector field and an iso-vorticity contour (magnitude 9 $s^{-1}$) are plotted at one time instant. For ease of comparison between the 3D SAPIV and two dimensional particle image velocimetry data, we normalize all lengths by the orifice diameter ($D_o$=30 mm), as known in the art. The origin of the X-Y-Z global coordinate system is placed approximately at the center of the outlet orifice of the vortex generator, with Y positive up and Z decreasing in the direction away from the cameras. In FIG. 11A the ring has propagated to a distance $Y/D_o \approx 3.72$ below the orifice outlet. Every vector in Z is plotted and every second vector is plotted in X and Y directions. The measured SAPIV volume is only limited by the volume which is illuminated by the laser. The iso-vorticity contour shows an incomplete ring, due to the fact that the ring is not centered in the laser volume and part of the ring is outside of the illuminated region. Cross sectional slices of vorticity, with planes at $Z/D_o$=0.003 and $X/D_o$=0, are plotted in FIG. 11B. As expected, isolated regions of vorticity are located where the ring passes through the planar cut in the three dimensional volume. The vorticity magnitude on the X-Z slice is slightly lower than for the X-Y, which is likely due to the lower resolution of the vector field in the Z-dimension. By locating the peaks in the normal vorticity component in each core cross-section on the plane passing through $Z/D_o$=0.003, the normalized diameter of the vortex is found to be $D/D_o$=0.77.

Figure 12:
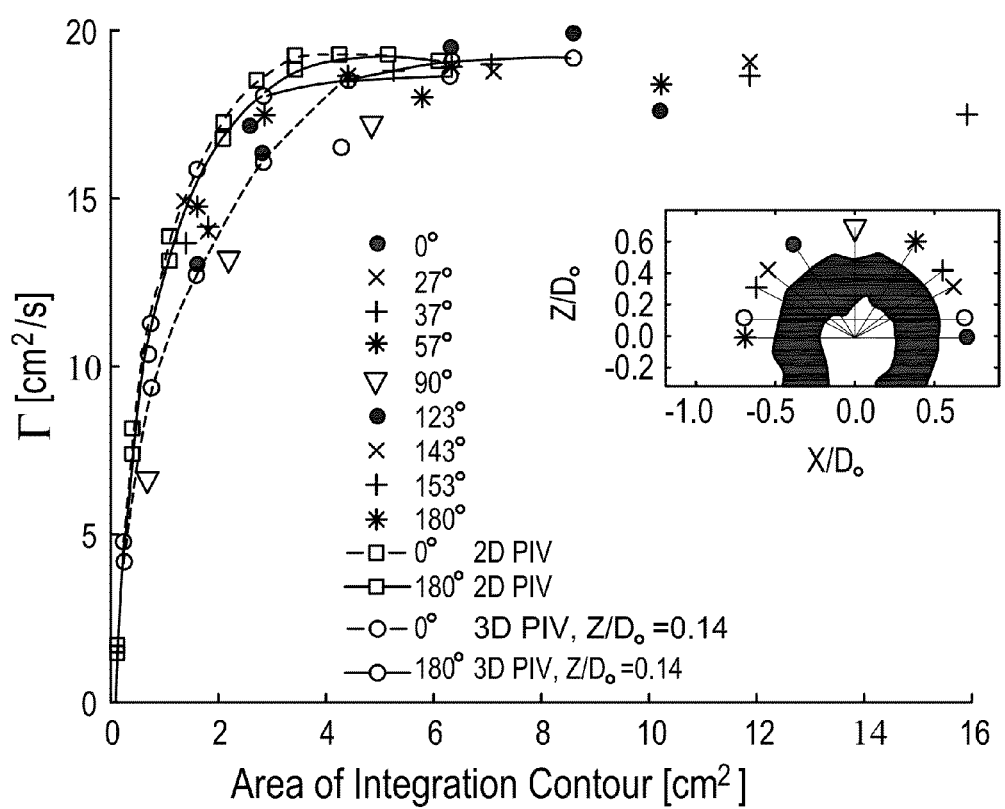
FIG. 12 is a diagram that shows the distribution of circulation as a function of area enclosed by integration contour on planar slices for several angles of the vortex ring.

Finally, to serve as another quantitative measure for benchmarking the 3D SAPIV system the circulation, Γ, is calculated on a variety of planes. The circulation is calculated by taking the line integral of velocity around a rectangular contour on a particular plane. Here, we calculate the circulation in two dimensional data, as well as on several planes for three dimensional data, using rectangular contours of increasing size to encompass up to one half of any two dimensional slice (i.e., encompassing one vortex core). Each contour is centered around the location of maximum surface-normal vorticity on the plane under consideration. The inset of FIG. 12 shows the location and angle of each plane on which circulation is computed. For the three dimensional data, nine planes are chosen with angles varying between 0°-180°, as well as one additional plane located at $Z/D_o$=0.11, on which the circulation is calculated for both cuts through the vortex ring core. FIG. 12 shows the circulation plotted against area enclosed by the integration contour for each plane.

For a symmetric vortex ring, the circulation on half of any one plane containing the axis passing through the ring center should be constant. From FIG. 12, it can be seen that the magnitude of circulation remains relatively constant regardless of plane angle, for a given integration contour size. The maximum difference in peak circulation is 2.69 $cm^2/s$ (13.5% of maximum) for the angled planes. On the plane passing through $Z/D_o$=0.11, as well as for the two dimensional data (laser plane at $Z/D_o$=0.15), the peak circulation is reached at a smaller integration contour size than for the planes passing through the central ring axis, because the bisected cross-sections are offset from the center of the ring. Nonetheless, the maximum circulation magnitude on the offset planes for both the two dimensional and three dimensional data is within 7% of the maximum found on the planes which pass approximately through the central axis of the ring.

The quantitative agreement between the 3D SAPIV data and the 2DPIV data confirms the viability of the SAPIV technique for making accurate measurements in three dimensional volumes. Although the simulations show the ability to reconstruct very densely seeded fields, the seeding density was kept rather low (0.026 ppp in the raw images) in this experiment to ensure proper reconstruction. However, it is expected that increased seeding density can be achieved in practice.

Synthetic aperture PIV offers a method for imaging complex three dimensional flow-fields with high seeding densities or significant phase differences and partial occlusions. SAPIV draws on the concept of light field imaging, which involves sampling and encoding many rays from a three dimensional scene, and is practically implemented with an array of cameras. Recombining the camera array images using synthetic aperture refocusing provides many desirable capabilities for three dimensional fluid flow measurement; namely, the ability to digitally refocus on isolated planes post-capture, to effectively "see-through" partial occlusions by exploiting the multiple camera viewpoints and to capture volumetric information at a single time instant. We expect the capabilities of the synthetic aperture system to be flexible enough to measure in other flow environments, such as multi-phase and bubbly flows or flows with partial obstructions.

Simulations showed that a single array arrangement allowed for measurement within volumes with depth ranging from 10 mm to 50 mm. Altering the optics on the cameras enables further scalability of the measurement range, as was shown in the simulation of the 100×100×100 $mm^3$ volume. In this manner, the behavior of the camera array is similar to the behavior of a single-lens camera: we have control over the viewable depth for a given magnification and can change the field of view by changing the magnification. Two simulated flow fields demonstrated the performance of the technique in resolving vector fields with high resolution and in a relatively large volume. The focal plane spacing of the system in the Z dimension, which is related to the depth of field, was theoretically derived for the simple model of two coplanar image sensors. The observed focal plane spacing in the simulations agreed extremely well with that predicted by the theory, despite the fact that the camera image sensors in the simulated model were not coplanar (the cameras were angled). This shows that the concise theory derived is an accurate and useful tool for predicting the depth of field of the refocused images as a function of camera baseline and optics.

The results of the three dimensional particle image velocimetry experiment indicate that SAPIV is a viable technique for efficiently and accurately resolving a range of three dimensional flow fields. In practice, the hardware implementation successfully captured an instantaneous three dimensional velocity vector field for a vortex ring, with only eight cameras, in a volume with an aspect ratio (Z:X-Y) that is comparable to some of the largest found in the literature. three dimensional SAPIV results compared well with the two dimensional particle image velocimetry experimental data for a similar vortex ring. The signal-to-noise ratio of plane of interest particles for each of the simulated cases was much lower than for the SAPIV experiment, indicating that seeding density can be greatly increased in future experimental studies, which will allow for increased vector resolution.

All data processing was performed on a commercially available personal computer. Reconstruction and three dimensional particle image velocimetry analysis was implemented in Matlab®; however, other available software could be used. However, the computation time to implement the map-shift-average algorithm, refocus and threshold the images, and assemble them into the reconstructed volume for two timesteps in the simulated 40×40×30 mm$^3$ volume required 15% of the time taken to compute the vector fields with 3 passes and 50% overlap (40 minutes to reconstruct the two timesteps, and 223 minutes to perform the PIV processing). For the SAPIV experiment, the time required to reconstruct the two volumes used to generate the three dimensional vector field (62 minutes) was 18% of the time required for the three dimensional particle image velocimetry processing of the fields (414 minutes). This attests to the relative simplicity of the refocusing algorithm. Therefore, the actual three dimensional particle image velocimetry calculations will dominate the computation time for synthetic aperture PIV.

It is believed that volume self-calibration can improve the image reconstruction quality and allow for increased seeding densities. The ability of the SAPIV technique to reconstruct the intensity fields without the use of volume self-calibration in the present study underscores the capability of the method. In addition, increasing the camera baseline spacing is expected to increase Z resolution. By increasing the baseline, the depth-of-field can be reduced allowing for more distinction between particles in the Z direction, which we expect will yield higher resolution in Z.

Synthetic Aperture PIV (SAPIV) provides a method for 3D-3C, quantitative flow velocimetry, which offers the ability to reconstruct very dense flow fields in relatively large volumes for a wide range of applications.

Figure 13:
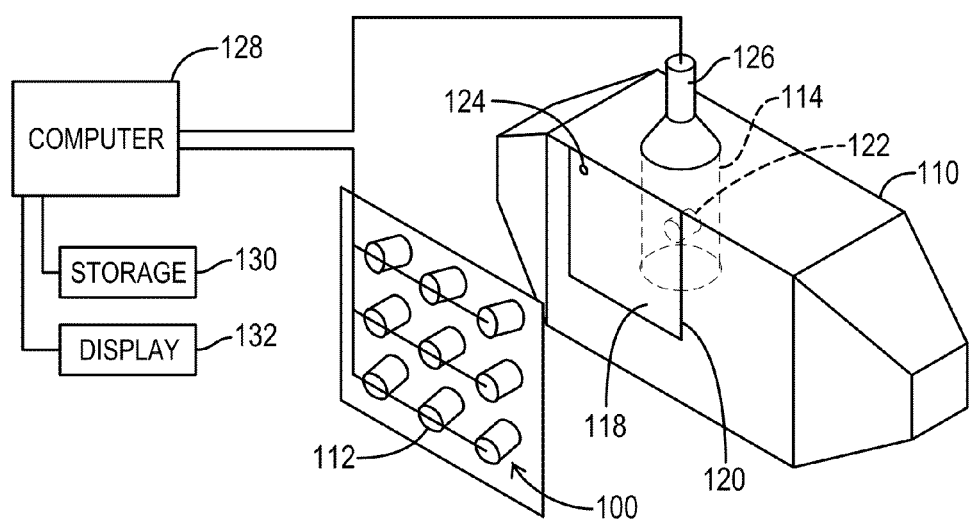
FIG. 13 is a diagram of an alternate embodiment of the invention using an array of cameras to monitor fluid flows in a water tunnel.

FIG. 13 is a diagram of an alternate embodiment of the invention using an array of cameras 100 to monitor fluid flows in a water tunnel 110. As shown, array of cameras 100 features nine digital cameras 112. Cameras 112 can be arranged in a plane or angled toward an area of interest. Area of interest 114 is in water tunnel 110. Array of cameras 100 is oriented proximate to water tunnel 110. Array 100 can either be in direct communication with water 118 in water tunnel 110 or separated from water tunnel 110 by a window 120. A test object 122 is positioned in area of interest 114. Water 118 in water tunnel 110 has particulate 124 distributed randomly therein at a predetermined concentration. Particle 124 concentration has been discussed in the preceding text. Area of interest 114 is illuminated by a light source 126. Light source 126 can be coherent or incoherent, continuous or strobed.

A computer 128 is provided for controlling and collecting data from the apparatus. Computer 128 can be joined to light source 126 in order to control actuation and strobing. Array 100 is joined to computer 128 in order to control and coordinate array 100 and to receive data from array 100. Computer 128 is joined to a storage device 130 and to a display device 132. Display device 132 allows direct user control of the apparatus. Display 132 can also allow direct viewing of data from array. Computer 128 can process the data as described in the preceding text or can communicate the data for further processing.

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. A synthetic aperture three dimensional fluid flow imaging apparatus, comprising:
a plurality of image recording devices, at least two of said plurality of image recording devices oriented so as to view a volume to be imaged along mutually non-parallel directions; and
a data processing apparatus based on a general purpose programmable computer configured to operate under control of a set of instructions recorded on a machine readable medium, said data processing apparatus when operating under control of said set of instructions configured to perform the steps of:
capturing a plurality of images using said at least two image recording devices oriented along mutually non-parallel directions to generate three dimensional intensity fields;
subtracting a sliding minimum value having a window size from the images;
convolving each image with a 3×3 Gaussian kernel;
equalizing a histogram of each image to a histogram of said image with the highest contrast;
increasing said contrast of each image by trimming a bottom range and a top range of intensity values;
subtracting a sliding minimum value having a window size from the images after the step of increasing said contrast to give a plurality of preprocessed images;
refocusing said plurality of preprocessed images on at least one refocus plane in the field of view of each image recording device to generate reconstructed three dimensional intensity fields on a plane placed at a location within said volume to be imaged;
performing intensity field cross-correlation on said reconstructed three dimensional intensity fields to extract therefrom velocity fields within said volume to be imaged, said velocity fields representing velocities of objects within said volume to be imaged; and
recording said velocity fields for later use.

2. The apparatus of claim 1, wherein said image recording devices are cameras.

3. The apparatus of claim 1, wherein said plurality of image recording devices are controlled by said general purpose programmable computer when operating under control of said set of instructions recorded on said machine readable medium.

4. The apparatus of claim 1, further comprising an illumination source configured to illuminate at least a portion of said volume within said volume to be imaged.

5. The apparatus of claim 4, wherein said illumination source is a laser.

6. The apparatus of claim 1, wherein a plurality of images captured simultaneously is used to derive said velocity fields within said volume to be imaged.

7. The apparatus of claim 1, wherein the volume to be imaged comprises a volume of flowing fluid having particles entrained therein.

8. The apparatus of claim 1, wherein the volume to be imaged comprises a volume of flowing fluid having multiple phases of fluid therein.

9. The apparatus of claim 1, wherein the volume to be imaged comprises a volume of gas having liquid droplets moving therein.

10. A method of providing synthetic aperture three dimensional fluid flow imaging data, comprising the steps of:
- capturing a plurality of images using a plurality of image recording devices, at least two of said plurality of image recording devices oriented so as to view a region of interest along mutually non-parallel directions to generate three dimensional intensity fields;
- subtracting a sliding minimum value having a window size from the images;
- convolving each image with a 3×3 Gaussian kernel;
- equalizing a histogram of each image to a histogram of said image with the highest contrast;
- increasing said contrast of each image by trimming a bottom range and a top range of intensity values;
- subtracting a sliding minimum value having a window size from the images after the step of increasing said contrast to give a plurality of preprocessed images;
- refocusing said plurality of preprocessed images on at least one refocus planes in the field of view of each image recording device to generate reconstructed three dimensional intensity fields on a plane placed at a location within the imaged volume using a data processing apparatus based on a general purpose programmable computer, said data processing apparatus operating under control of a set of instructions recorded on a machine readable medium;
- performing intensity field cross-correlation on said reconstructed three dimensional intensity fields to extract velocity fields therefrom; and
- recording said velocity fields for later use.

11. The method of claim 10, wherein said bottom range and said top range of intensity values are 0.1% of said intensity values.

12. The method of claim 10, wherein the region of interest comprises a volume of flowing fluid having particles entrained therein.

13. The method of claim 10, wherein the region of interest comprises a volume of flowing fluid having multiple phases of fluid therein.

14. The method of claim 10, wherein the volume to be imaged comprises a volume of gas having liquid droplets moving therein.

* * * * *